United States Patent
Joo et al.

(10) Patent No.: US 12,215,172 B2
(45) Date of Patent: *Feb. 4, 2025

(54) BIO-RESPONSIVE ADHESIVE ANTIBODY DELIVERY PLATFORM FOR IMMUNOTHERAPY AND PREPARATION METHOD THEREOF

(71) Applicant: Postech Academy-Industry Foundation, Gyeongsangbuk-do (KR)

(72) Inventors: Kye Il Joo, Daegu (KR); Hyung Joon Cha, Gyeongsangbuk-do (KR); Yeon Su Jeong, Gyeongsangbuk-do (KR)

(73) Assignee: POSTECH ACADEMY-INDUSTRY FOUNDATION, Pohang-si (KR)

( * ) Notice: Subject to any disclaimer, the term of this patent is extended or adjusted under 35 U.S.C. 154(b) by 672 days.

This patent is subject to a terminal disclaimer.

(21) Appl. No.: 17/065,368

(22) Filed: Oct. 7, 2020

(65) Prior Publication Data
US 2021/0139608 A1 May 13, 2021

(30) Foreign Application Priority Data
Oct. 14, 2019 (KR) .................. 10-2019-0127048

(51) Int. Cl.
*C07K 16/44* (2006.01)
*A61K 45/00* (2006.01)

(52) U.S. Cl.
CPC ............. *C07K 16/44* (2013.01); *A61K 45/00* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 7,622,550 B2 | 11/2009 | Cha et al. |
| 7,947,806 B2 | 5/2011 | Cha et al. |
| 8,173,395 B2 | 5/2012 | Cha et al. |
| 2005/0084456 A1 | 4/2005 | Tang et al. |
| 2007/0014773 A1 | 1/2007 | Matheny et al. |
| 2009/0105449 A1 | 4/2009 | Tomich et al. |
| 2009/0151600 A1* | 6/2009 | Cha .................. C07K 14/43504 530/344 |
| 2009/0203883 A1 | 8/2009 | Cha et al. |
| 2010/0120923 A1 | 5/2010 | Stewart et al. |
| 2013/0052712 A1 | 2/2013 | Cha et al. |
| 2013/0323249 A1* | 12/2013 | Zhou .................. C07K 16/2827 530/387.3 |
| 2014/0023594 A1 | 12/2014 | Park et al. |
| 2015/0252148 A1* | 9/2015 | Lee ................... A61L 27/56 435/395 |
| 2016/0017279 A1 | 1/2016 | Cha et al. |
| 2017/0231999 A1* | 8/2017 | Balog ................. C07C 275/40 424/133.1 |

FOREIGN PATENT DOCUMENTS

| | | |
|---|---|---|
| JP | 61-085400 | 4/1986 |
| JP | 09-225019 | 9/1997 |
| JP | 2009-084224 | 4/2009 |
| KR | 10-2011-0007672 | 1/2011 |
| KR | 10-2012-0013626 | 2/2012 |
| KR | 10-2013-0021951 | 3/2013 |
| KR | 10-1311325 | 9/2013 |
| KR | 10-2014-0027031 | 3/2014 |
| KR | 10-2016-0026441 | 3/2016 |
| KR | 10-2016-0037413 | 4/2016 |
| KR | 10-2016-0110864 | 9/2016 |
| KR | 10-2016-0129982 | 11/2016 |
| KR | 10-2017-0108052 | 9/2017 |
| WO | 2005092920 | 10/2005 |
| WO | 2006107183 | 10/2006 |
| WO | 2008150101 | 12/2008 |
| WO | 2009029406 | 3/2009 |
| WO | 2009094060 | 7/2009 |

OTHER PUBLICATIONS

Xu, Shijie et al. International journal of nanomedicine vol. 14 17-32. Dec. 18, 2018, doi:10.2147/IJN.S175340 (Year: 2018).*
Janeway, Charles A. "Immunobiology: The Immune System in Health and Disease." 2001 (Year: 2001).*
Joo, Kye Il, et al. Biomaterials 263 (2020): 120380 (Year: 2020).*
Stryer, Biochemistry 4th, WH Freeman, New York. 1995 (Year: 1995).*
Colman, Research in Immunology 145.1 (1994): 33-36 (Year: 1994).*
Chen, Weikai et al. Gels (Basel, Switzerland) vol. 7,4 199. Nov. 5, 2021, doi:10.3390/gels7040199 (Year: 2021).*
Jeong, Yeonsu, et al. ACS nano 12.9 (2018): 8909-8919 (Year: 2018).*
(Zhu, Lin, et al. Proceedings of the National Academy of Sciences 110.42 (2013): 17047-17052 (Year: 2013).*
Spahn, Jessica, et al. Journal for immunotherapy of cancer 3.2 (2015): 1-1 (Year: 2015).*
Marabelle, A., et al. Annals of Oncology 28 (2017): xii33-xii43.), (Year: 2017).*
Kim, Biomaterials 72 (2015) 104-111 (Year: 2015).*

(Continued)

*Primary Examiner* — Michael Szperka
*Assistant Examiner* — Lia E Taylor
(74) *Attorney, Agent, or Firm* — LEX IP MEISTER, PLLC

(57) ABSTRACT

Disclosed are a bio-responsive adhesive antibody delivery platform for immunotherapy, use thereof, and a preparation method thereof. The bio-responsive adhesive antibody delivery platform for immunotherapy according to the present disclosure may enhance a retention time of the antibody at a target site via adhesiveness of the delivery platform and may selectively release the antibody in response to specific enzymes to efficiently deliver the antibody.

12 Claims, 38 Drawing Sheets

Specification includes a Sequence Listing.

(56) References Cited

OTHER PUBLICATIONS

Kim et al., "Mussel-Inspired Protein Nanoparticles Containing Iron(III)-DOPA Complexes for pH-Responsive Drug Delivery", Angewandte Chemie International Edition, 2015, 54, pp. 7318-7322.
Qiao et al., "Kidney-specific drug delivery system for renal fibrosis based on coordination-driven assembly of catechol-derived chitosan", Biomaterials, 2014, 35, pp. 7157-7171.
Kim et al., "Mussel-inspired adhesive protein-based electrospun nanofibers reinforced by Fe(III)-DOPA complexation", J Mater Chem B, 2015, 3, pp. 112-118.
Kim et al., "Mussel-mimetic protein-based adhesive hydrogel", Biomacromolecules, 2014, 15, pp. 1579-1585.
Zeng et al., "Strong reversible Fe3+-mediated bridging between dopa-containing protein films in water", PNAS, 2010, 107(29), pp. 12850-12853.
Sridhar et al., "Electrosprayed nanoparticles for drug delivery and pharmaceutical applications", Biomatter, 2013, 3(3), pp. e24281-1-e24281-12.
Harrington et al., "Iron-clad fibers: a metal-based biological strategy for hard flexible coatings", Science, 2010, 328, pp. 216-220.
Kruif et al., "Complex coacervation of proteins and anionic polysaccharides", Current Opinion in Colloid and Interface Science, 2004, 9(5), pp. 340-349.
Hwang et al., "Cell adhesion biomaterial based on mussel adhesive protein fused with RGD peptide", Biomaterials, 2007, 28(28), pp. 4039-4046.
Hwang et al., "Practical recombinant hybrid mussel bioadhesive fp-151", Biomaterials, 2007, 28(24), pp. 3560-3568.
Hwang et al., "Recombinant mussel adhesive protein Mgfp-5 as cell adhesion biomaterial", Journal of Biotechnology, 2006, 127(4), pp. 727-735.
Hwang et al., "Expression of functional recombinant mussel adhesive protein Mgfp-5 in *Escherichia coli*", Applied and Environmental Microbiology, 2004, 70(6), pp. 3352-33593.
European Patent Office, European search report of the corresponding European Patent Application No. 10812172.4, Aug. 7, 2013.
Hwang et al., "Viscosity and interfacial properties in a mussel-inspired adhesive coacervate", Soft Matter, 2010, 6(14), pp. 3232-3236.
Taylor, "Chemoenzymatic Synthesis of Peptidyl 3,4-Dihydroxyphenylalanine for Structure-Activity Relationships in Marine Invertebrate Polypeptides", Analytical Biochemistry, 2002, 302, pp. 70-74.
Mathiowitz, "Bioadhesive Drug Delivery Systems: Fundamentals, Novel Approaches, And Development", Marcel Dekker, 1999.
Hwang et al., "Promotion of osteoblast proliferation on complex coacevation-based hyaluronic acid-recombinant mussel adhesive protein coatings on titanium", Biomaterials, 2010, 31, pp. 1080-1084.
Lim et al., "Complex Coacervation of Mussel Adhesive Protein with Hyaluronic Acid for microencapsulated bioadhesive system", Trend of Biotechnology and Bioengineering XXV, K109, The Korean Society for Biotechnology and Bioengineering, 2009, pp. 127.
Holten-Andersen et al., "Stiff Coatings on Compliant Biofibers: The Cuticle of Mytilus californianus Byssal Threads", Biochemistry, 2009, 48, pp. 2752-2759.
Lim et al., "The adhesive properties of coacervated recombinant hybrid mussel adhesive proteins", Biomaterials, 2010, 31, pp. 3715-3722.
Cai et al., "Porous microsphere and its applications", Int J Nanomed, 2013, 8, pp. 1111-1120.
Nihant et al., "Microencapsulation by cacervation of poly(lactide co glyolide) III characterization of the final microspheres", Polymer Int, 1994, 34, pp. 289-299.
Xu, "Mussel-Inspired Mucoadhesive hydrogels for drug delivery", Department of Mining and Materials Engineering, McGill University, 2015, pp. 1-212.
Kim et al., "Dopamine-Induced Mineralization of Calcium Carbonate Vaterite Microspheres", Langmuir, 2010, 26(18), pp. 14730-14736.
Brubaker et al., "Enzymatically degradable mussel-inspired adhesive hydrogel", Biomacromolecules, 2011, 12, pp. 4326-4334.
Lee et al., "Synthesis of 3,4-dihydroxyphenylalanine (DOPA) containing monomers and their co-polymerization with PEG-diacrylate to form hydrogels", Journal of Biomaterials Science, 2004, 15(4), pp. 449-464.
Yang et al., "Development of highly porous large PLGA microparticles for pulmonary drug delivery", Biomaterials, 2009, 30, pp. 1947-1953.
Kim et al., "Droplet microfluidics for producing functional microparticles", Langmuir, 2014, 30, pp. 1473-1488.
Jo et al., "Mussel protein-based sticky porous microspheres as an injectable stem cell carrier with vascularization capacity", Abstract, 2017, pp. 1-4.
Coleman, "Types of Heparin", (Sep. 28, 2010) http://www.livestrong.com/article/252722-types-of-heparin/.
Fan et al., "Light-responsive biodegradable nanomedicine overcomes multidrug resistance via NO-enhanced chemosensitization", ACS Applied Materials & Interfaces, 2016, 8(22), pp. 13804-13811.
Kao et al., "Controllable NO release from Cu 1.6 S nanoparticle decomposition of S-nitroglutathiones following photothermal disintegration of polymersomes to elicit cerebral vasodilatory activity", Chemical Science, 2017, 8(1), pp. 291-297.
Jeong et al., "Mussel Protein-Based Photo-Activated Nanosystem for Synergisitc Cancer Therapy", 2019, Spring Meeting The KSBM, abstract only.
Jeong et al., "Photothermal-activated mussel adhesive protein nanoparticles for synergisite cancer therapy", 2019, KSBB Spring Meeting and International Symposium, abstract only.
Jeong et al., "Mussel protein nanoparticle-mediated photo-responsive system for cancer-specific photothermal-chemotherapy", TERMIS EU, May 27 to 31, 2019, Rhodes, Greece.
Jeong et al., "Bioinspired Protein-Based Laser-Activated Nanotherapy for Synergistic Cancer Treatment", TERMIS-AP, 2019.
Lee et al., "MMPs-specific PEGylated peptide-DOX conjugate micelles that can contain free doxorubicin", European Journal of Pharmaceutics and Biopharmaceutics, 2007, 67, pp. 646-654.
Long et al., "Epacadostat plus pembrolizumab versus placebo plus pembrolizumab in patients with unresectable or metastatic melanoma (ECHO-301/KEYNOTE-252): a phase 3, randomized, double-blind study", Lancet Oncol, 2019, 20, pp. 1083-1097.

* cited by examiner

BIO-RESPONSIVE ADHESIVE ANTIBODY DELIVERY PLATFORM FOR IMMUNOTHERAPY AND PREPARATION METHOD THEREOF

CROSS-REFERENCE TO RELATED APPLICATIONS

This application is based on and claims priority from Korean Patent Application No. 10-2019-0127048, filed on Oct. 14, 2019, with the Korean Intellectual Property Office, the disclosure of which is incorporated herein in its entirety by reference.

TECHNICAL FIELD

The present disclosure relates to a bio-responsive adhesive antibody delivery platform for immunotherapy, use thereof, and a preparation method thereof.

BACKGROUND

Immunotherapy, which treats diseases by regulating our body's immune system, is currently on the spotlight as an advanced treatment. Particularly, it is actively used as an anti-cancer immunotherapy and immunosuppressive therapy after tissue or organ transplantation. Particularly, in the treatment of cancer, chemotherapy or radiation treatment is frequently performed, but the treatment is limited due to side effects in normal cells. Therefore, research on immunotherapy capable of attacking only target cells while normal cells are not affected has been actively conducted. In immunotherapy, antibody treatment is a method of treatment by administering an antibody (Ab) produced in vitro to the human body for the purpose of treatment and thus controlling the immune system. In the anti-cancer treatment, the antibody treatment may more effectively treat the cancer by increasing the activity of immune cells against cancer cells, as well as may reduce the immune response to external therapeutic materials via immunosuppressive therapy to prevent tissue and transplant rejection.

However, when a large amount of antibody is continuously administered, side effects caused by nonspecific binding to normal cells and tissues occur. Particularly, there is a problem of autoimmune via inducing off-targeting and over-activation of immune cells due to the release of too much antibody. Further, when administering the antibody to the target site for topical treatment, most of the antibody flows out of the target site by blood, etc. Thus, it is difficult to obtain effective therapeutic efficacy. Therefore, it is necessary to develop an antibody delivery platform that may improve the maintenance time of the antibody at the target site.

In order to induce effective antibody action, the antibody delivery platform not only increases the retention time of the antibody at the target site, but also must efficiently release the antibody. To this end, a delivery platform has been developed with a controlled release system that may automatically control the release of antibodies via stimulation in cells such as pH, redox potential, or enzymes. In particular, the enzyme responsive system that induces release of the antibodies by separating antibodies from the delivery platform using an enzyme specifically expressed at the target site may develop a delivery platform tailored to various target enzymes unlike other stimuli, and thus may be applied to the treatment of various diseases.

Mussel has excellent adhesion force in underwater using the adhesive protein present in the byssus. The mussel adhesive protein (MAP) performs effective underwater adhesion based on electrical interaction, hydrogen bonding, or covalent bonding via amino acids such as lysine or DOPA (3,4-dihydroxyphenylalanine) and may adhere to the tissue surface even in a living body with a moisture environment. Further, the MAP is actively researched as a medical material because the MAP has high biocompatibility and biodegradability and does not induce an immune response. Cases have been reported that the MAP is used as underwater adhesives to treat various diseases such as bone binder, skin suture, or bladder fistula treatment. In addition, there have been reported cases that the MAP is prepared as an adhesive nanoparticle and is used as a local drug delivery platform.

However, there has been no attempt to prepare or apply a bio-responsive antibody delivery platform using the mussel adhesive protein.

SUMMARY

As a result, the present inventors tried to develop a bio-responsive antibody delivery platform using the mussel adhesive protein. As a result, the bio-responsive adhesive antibody delivery platform was prepared by bonding the mussel adhesive protein and a peptide cleavable by MMP2 to each other. It was identified that the antibody delivery platform increased the retention time of the antibody at the target site via the adhesive of mussel adhesive protein, and when the platform is cleaved by the MMP2 enzyme, the platform may automatically separate antibodies from the intracellular environment and release the antibodies. Thus, the present disclosure was completed.

The present disclosure has been made in an effort to provide a bio-responsive adhesive antibody delivery platform containing a mussel adhesive protein (MAP) and peptides cleavable by MMP2 (matrix metalloproteinase-2) conjugated to the MAP.

Further, the present disclosure has been made in an effort to provide an immunotherapy composition containing the bio-responsive adhesive antibody delivery platform and an antibody.

Further, the present disclosure has been made in an effort to provide a pharmaceutical composition for prevention or treatment of cancer, the pharmaceutical composition containing the immunotherapy composition.

Further, the present disclosure has been made in an effort to provide a method for preparing the bio-responsive adhesive antibody delivery platform.

Further, the present disclosure has been made in an effort to provide a method for preparing the immunotherapy composition.

An exemplary embodiment of the present disclosure provides a bio-responsive adhesive antibody delivery platform containing a mussel adhesive protein (MAP) and peptides cleavable by MMP2 (matrix metalloproteinase-2) conjugated to the MAP.

Another exemplary embodiment of the present disclosure provides an immunotherapy composition containing the bio-responsive adhesive antibody delivery platform and an antibody.

Still another exemplary embodiment of the present disclosure provides a pharmaceutical composition for preventing or treating cancer containing the immunotherapy composition.

Still another exemplary embodiment of the present disclosure provides an anti-cancer adjuvant containing the immunotherapy composition.

Still another exemplary embodiment of the present disclosure provides a preparation method of a bio-responsive adhesive antibody delivery platform, the method including covalently bonding a mussel adhesive protein to a C terminus of a peptide cleavable by MMP2 (matrix metalloproteinase-2).

Still another exemplary embodiment of the present disclosure provides a method for preparing an immunotherapy composition, the method including covalently bonding an antibody to an N terminus of a peptide cleavable by MMP2 (matrix metalloproteinase-2); and covalently bonding a mussel adhesive protein to a C terminus of the MM2 cleavable peptide having the antibody binding thereto.

According to the exemplary embodiments of the present disclosure, the bio-responsive adhesive antibody delivery platform for immunotherapy according to the present disclosure may enhance the retention time of the antibody at the target site via the adhesiveness of the delivery platform and may selectively release the antibody in response to specific enzymes to efficiently deliver the antibodies The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 2A is a diagram showing the emission spectrum of free Ab (Alexa488-labeled Ab), a simple mixture of MAP and Ab, and MAP conjugated Ab (MAP-Ab). FIG. 2B is a diagram showing the emission spectrum of MAP-Ab with or without MMP2. FIG. 2C is a diagram comparing the results of QCM analysis of MAP-Ab and free Ab at 200 µl/min flow rate. FIG. 2D is a diagram showing the outline (left) and the measurement result (right) of measuring the surface adhesion force of free Ab and MAP-Ab in the asymmetric mode of SFA. FIG. 2E is a diagram showing the surface adhesion force of free Ab and MAP-Ab measured by SFA (**$p<0.01$, error bar means the standard error of the average).

FIG. 2F is a diagram showing the optical (top) and fluorescence (bottom) imaging results of the swine skin tissue surface after spraying MAP-Ab (green, Alexa488-labeled Ab).

FIG. 3A shows the results of QCM analysis. FIG. 3B shows the fluorescence image of the MAP-Ab-sprayed glass surface, and the green signal indicates Alexa488-labeled Ab (scale bar=100 µm).

FIG. 4A shows that MAP-Ab sprayed on a glass surface remains stable in PBS for 7 days, whereas the addition of MMP2 on day 7 easily induces Ab release (scale bar=100 µm). FIG. 4B is a diagram showing the cumulative Ab release profile from MAP-Ab in the presence or absence of MMP2.

FIG. 5A is a diagram showing the in vivo fluorescence imaging results of mice at each time point after subcutaneous injection of free Ab (Alexa488-labeled Ab) and MAP conjugated to Ab (MAP-Ab). FIG. 5B shows the average integrated fluorescence intensity (n=3) (*$p<0.05$, **$p<0.01$, error bar indicates the standard error of the average). FIG. 5C is a diagram showing serum levels of Alexa488-labeled Ab measured at 6 and 24 hours after subcutaneous injection of free Ab and MAP-Ab. FIG. 5D is a diagram showing the immunofluorescence image of tumor sections on 7 days after treatment with free aPD-L1 and MAP-aPD-L1 (purple: aPD-L1, blue: nucleus). FIG. 5E is a diagram showing a confocal image of MDA-MB 231 cancer cells co-cultured with MMP2-treated or -untreated MAP-aPD-L1 in a transwell system. Green and blue signals indicate aPD-L1, cell membrane and nucleus, respectively (scale bar=20 µm).

FIG. 6A shows the transwell structure used to identify the bioactivity of aPD-L1 released in the presence of MMP2. MAP-aPD-L1 together with PBS or PBS containing MMP2 was placed in an upper compartment, and cancer cells were cultured in a lower compartment. FIG. 6B shows a confocal image of B16F10 cancer cells co-cultured with MAP-aPD-L1 treated or untreated with MMP2 in a transwell system. Red, green and blue signals indicate aPD-L1, cell membrane and nucleus, respectively (scale bar=20 µm).

FIG. 7A: Schematic illustration of localized immunotherapy using the B16F10 murine melanoma model. FIG. 7B: Individual tumor growth curves of the different treatment groups as indicated (n=6). FIG. 7C: Average tumor growth curves of the different treatment groups as indicated (n=6). Error bars represent the standard error of the mean ($p<0.01$, *$p<0.005$). FIG. 7D: Representative tumor sizes in the PBS-, aPD-L1- and MAP-aPD-L1-treated groups on day 21. FIG. 7E: Analysis of tumor weights in the PBS-, aPD-L1- and MAP-aPD-L1-treated groups as measured during the end point analysis. FIG. 7F: Survival curves of the mice that received different treatments.

FIG. 8A: The experimental protocol using the B16F10 melanoma mouse model. FIG. 8B: Immunofluorescence images of B16F10 tumor sections exhibiting $CD4^+$ and $CD8^+$ T cell infiltration into the tumor (red: $CD4^+$ T cells, yellow: $CD8^+$ T cells, blue: nucleus, scale bar=20 µm). FIG. 8C: Representative FACS plots of $CD4^+$ and $CD8^+$ tumor-infiltrating lymphocytes (TILs) isolated from tumors treated as indicated. FIG. 8D: Intracellular staining of the cytokine IFN-γ in $CD8^+$T cells isolated from TILs that were stimulated with PMA and ionomycin for 6 hours. FIG. 8E: Flow cytometric analysis of $CD4^+$ $Foxp3^+$ T cells within TILs. FIG. 8F: Quantitative analysis of $CD4^+$ and $CD8^+$ T cells according to FIG. 8C (n=10 for the PBS and MAP-aPD-L1 treatment group, n=8 for the aPD-L1 treatment group). Error bars represent the standard error of the average (*$p<0.05$, $p<0.01$, *$p<0.005$). FIG. 8G: Quantitative analysis of $CD8^+$ T cells according to FIG. 8D (n=10 for the PBS and MAP-aPD-L1 treatment group, n=8 for the aPD-L1 treatment group). Error bars represent the standard error of the average (*p<0.05, p<0.01, *p<0.005). FIG. 8H: Quantitative analysis of CD4+ Foxp3+ T cells according to FIG. 8E, (n=10 for the PBS and MAP-aPD-L1 treatment group, n=8 for the aPD-L1 treatment group). Error bars represent the standard error of the average (*p<0.05, p<0.01, *p<0.005).

FIG. 9A: Schematic illustrating a protocol of imuGlue therapy combined with 1-MT in the B16F10 mouse melanoma model. FIG. 9B: Individual tumor growth curves from the different treatment groups (n=6). Error bars represent the standard error of the average (*p<0.05, **p<0.01). FIG. 9C: Average tumor growth curves from the different treatment groups (n=6). Error bars represent the standard error of the average (*p<0.05, **p<0.01). FIG. 9D: Average body weights over the duration of the experiment. FIG. 9E: Representative immunofluorescence images of tumor sections from mice of different treatment groups showing CD8+ T cell infiltration into the tumor (scale bar=20 μm).

DETAILED DESCRIPTION

Figure 1:
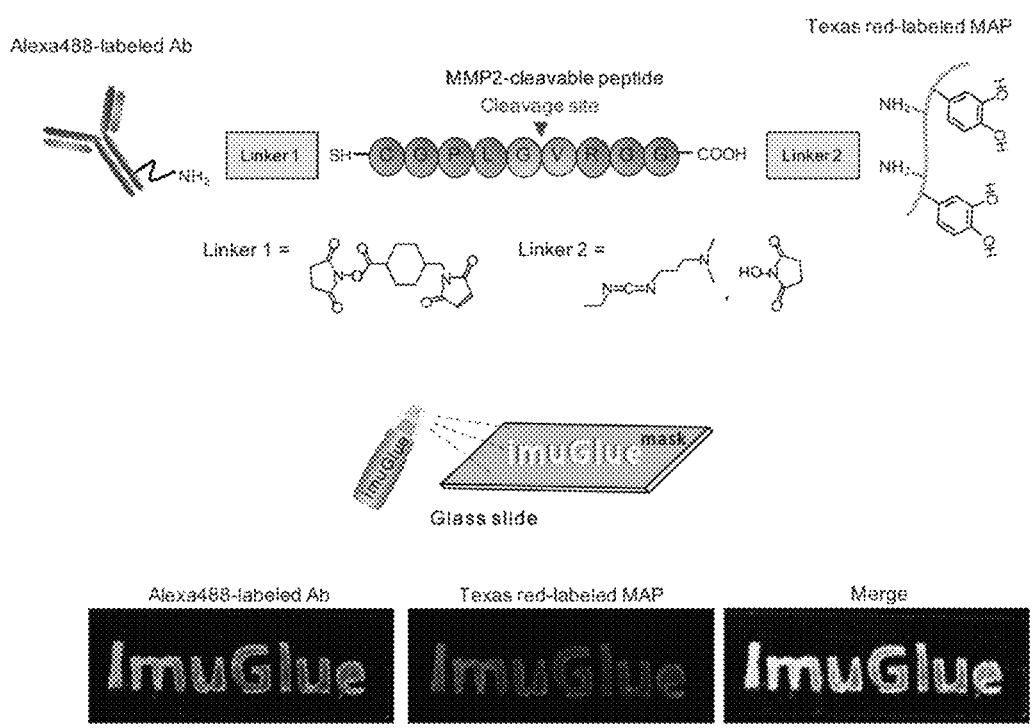
FIG. 1 is a diagram schematically showing imuGlue prepared by covalently bonding the mussel adhesive protein (MAP) to Ab (antibody).

In the following detailed description, reference is made to the accompanying drawing, which forms a part hereof. The illustrative embodiments described in the detailed description, drawing, and claims are not meant to be limiting. Other embodiments may be utilized, and other changes may be made, without departing from the spirit or scope of the subject matter presented here.

Hereinafter, the present disclosure will be described in detail.

The present disclosure provides a bio-responsive adhesive antibody delivery platform containing a mussel adhesive protein (MAP) and peptides cleavable by MMP2 (matrix metalloproteinase-2) conjugated to the MAP.

According to the present disclosure, the peptide (MMP2-cleavable peptide) cleavable by the MMP2 acts as a linker connecting the antibody and mussel adhesive protein to each other, and is decomposed by MMP2 (matrix metalloproteinase-2) enzyme overexpressed in cancer cells, thereby allowing the antibody delivery platform to selectively release antibodies in a tumor microenvironment.

The peptide cleavable by the MMP2 may be appropriately selected by those skilled in the art to which the present disclosure belongs. Preferably, the MMP2-cleavable peptide may be a peptide composed of 5 to 10 amino acids containing a peptide bond that is cleavable by MMP2. For example, the peptide may be any one of peptides composed of an amino acid sequence including CGPLGVRGG (SEQ ID NO: 12), GPVGLIGK (SEQ ID NO: 13), GPLGIAGQ (SEQ ID NO: 14), GPLGV (SEQ ID NO: 15) or PVGLIG (SEQ ID NO: 16), but is not limited thereto.

In one embodiment of the present disclosure, a peptide composed of the amino acid sequence represented by Cys-Gly-Pro-Leu-Gly-Val-Arg-Gly-Gly (C-G-P-L-G-V-R-G-G, SEQ ID NO: 12) may be used. The Gly-Val (G-V) peptide bond of the peptide composed of the amino acid sequence represented by the SEQ ID NO: 12 may be cut by the MMP2 enzyme, such that the peptide may be used as a peptide linker in the bio-responsive adhesive antibody delivery platform according to the present disclosure.

According to the present disclosure, the antibody delivery platform may additionally contain a linker at the C terminus of the peptide cleavable by MMP2. In one embodiment of the present disclosure, EDC (1-ethyl-3-(3-dimethylaminopropyl)carbodiimide) and NHS (N-hydroxysuccinimide) may be used as the linker.

TABLE 1

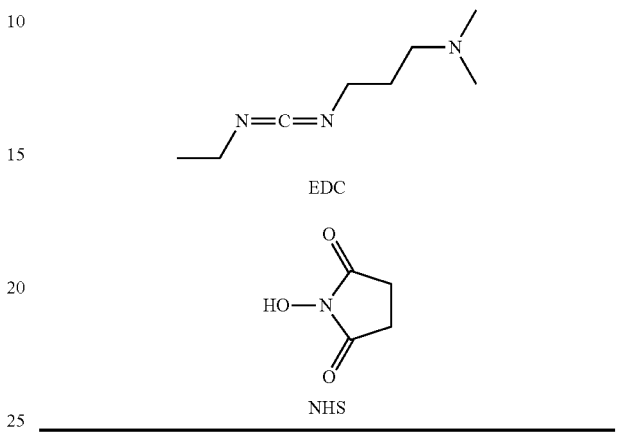

EDC

NHS

According to the present disclosure, the "mussel adhesive protein (MAP)" is an adhesive protein derived from mussel. Preferably, the MAP may include a mussel adhesive protein derived from *Mytilus edulis, Mytilus galloprovincialis* or *Mytilus coruscus*, or a variant thereof, but is not limited thereto.

For example, the mussel adhesive protein of the present disclosure may include Mefp (*Mytilus edulis* foot protein)-1, Mefp-2, Mefp-3, Mefp-4, Mefp-5, Mgfp (*Mytilus galloprovincialis* foot protein)-1, Mgfp-2, Mgfp-3, Mgfp-4 and Mgfp-5, Mcfp (*Mytilus coruscus* foot protein)-1, Mcfp-2, Mcfp-3, Mcfp-4, and Mcfp-5 or variants thereof as derived from the mussel species, respectively. Preferably, the mussel adhesive protein of the present disclosure may include a protein selected from the group consisting of fp-1 (SEQ ID NO: 1), fp-2 (SEQ ID NO: 2), fp-3 (SEQ ID NO: 3), fp-4 (SEQ ID NO: 4), fp-5 (SEQ ID NO: 5) and fp-6 (SEQ ID NO: 6), or a fusion protein to which one or more proteins selected from the group are linked, or a variant of the protein. However, the present disclosure is not limited thereto.

Further, the mussel adhesive protein of the present disclosure may include all of the mussel adhesive proteins as described in WO2006/107183 or WO2005/092920. Preferably, the mussel adhesive protein may be one or more selected from the group consisting of fp-151 (SEQ ID NO: 7), fp-131 (SEQ ID NO: 8), fp-353 (SEQ ID NO: 9), fp-153 (SEQ ID NO: 10) and fp-351 (SEQ ID NO: 11), but is not limited thereto.

Further, the mussel adhesive protein may contain additional sequences at the carboxyl or amino terminus of the mussel adhesive protein, or some amino acids may be substituted with other amino acids as long as the adhesion force thereof is maintained. Preferably, a polypeptide composed of 3 to 25 amino acids containing RGD (Arg-Gly-Asp) may be linked to the carboxyl or amino terminus of the mussel adhesive protein but is not limited thereto.

Further, in accordance with the present disclosure, in the mussel adhesive protein, 10 to 100% of total tyrosine residues may be modified to DOPA (3,4-dihydroxyphenylalanine, DOPA). Tyrosine accounts for about 20 to 30% of the total amino acid sequence of most mussel adhesive proteins. Tyrosine in the natural mussel adhesive protein is converted to a form of DOPA via adding —OH group thereto through hydration process. However, in the mussel adhesive protein produced in E. coli, the tyrosine residues are not modified. Thus, the mussel adhesive protein produced in E. coli may be subjected to a modification reaction that converts tyrosine residues to DOPA via separate enzyme and chemical treatment methods. The method for modifying the tyrosine residue contained in the mussel adhesive protein to DOPA may use a method known in the art and is not particularly limited. Preferably, tyrosine residues may be modified to DOPA residues using tyrosinase. In one embodiment of the present disclosure, the mussel adhesive protein that satisfies the above DOPA conversion may be produced via an in vitro enzyme reaction using mushroom tyrosinase.

The bio-responsive adhesive antibody delivery platform according to the present disclosure contains the mussel adhesive protein that possesses unique underwater adhesion force, thereby enhancing the retention time of the antibody at the target site. The bio-responsive adhesive antibody delivery platform may react with MMP2 to selectively separate and release the antibody therefrom such that the antibody may be efficiently delivered.

Further, the present disclosure provides an immunotherapy composition containing the bio-responsive adhesive antibody delivery platform according to the present disclosure and an antibody. In one embodiment of the present disclosure, bioengineered MAP is covalently conjugated to aPD-L1 via a peptide linker (SEQ ID NO: 12) that is cleavable by MMP2. The antibody delivery platform having the antibody conjugated thereto is named "imuGlue" which is used in the experiment.

According to the present disclosure, the antibody may be directly coupled to or may be coupled, via a linker, to a cysteine located at the N terminus of the peptide cleavable by MMP2. In an embodiment of the present disclosure, Sulfo-SMCC is added to the antibody (Ab) and the mixture is stirred, and then a peptide that may be cleaved by MMP2 is added to the mixture. The produced mixture is further cultured with EDC and NHS to prepare the imuGlue according to the present disclosure.

TABLE 2

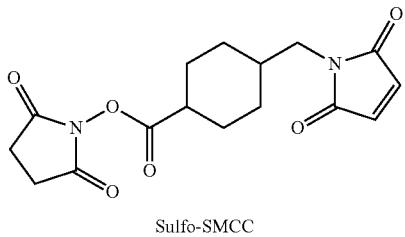 [SMILES: O=C(ON1C(=O)CCC1=O)C1CCC(CN2C(=O)C=CC2=O)CC1]

Sulfo-SMCC

According to the present disclosure, the antibody may be used without limitation as long as the antibody may be conjugated with a bio-responsive adhesive antibody delivery platform according to the present disclosure via covalent bonding between an amine group present in the antibody and the linker. For example, the antibody may be one or more selected from the group consisting of monoclonal antibodies, bispecific antibodies, chimeric antibodies, human antibodies and humanized antibodies. In addition, modified antibodies such as bispecific antibodies or antibody fragments may be used. The term "antibody fragment" means a fragment that possesses the binding function to at least antigen. The antibody fragment may include short chain antibodies, diabody, triabodies, tetrabodies, Fab fragments, F(ab')2 fragments, Fd, scFv, domain antibodies, minibodies, single chain antibodies (scAb), derivatives of antibody constant region, and artificial antibody based on protein scaffolds.

Optionally, the antibody may be selected from the group consisting of IgA, IgD, IgE, IgG and IgM.

The antibodies may have a binding ability and specificity to cancer specific antigens, cell surface receptor proteins, cell surface proteins, transmembrane proteins, signaling proteins, cell survival regulators, cell proliferation regulators, molecules associated with tissue development or differentiation, lymphokines, cytokine, a molecule involved in cell cycle regulation, and a molecule related to angiogenesis or a molecule related to vascularization. Preferably, the antibody may have a binding ability and specificity to a cancer specific antigen.

Preferably, the antibody may include immune checkpoint inhibitors (ICI) which inhibits the surface proteins (e.g., PD-L1, PD-L2, etc.) of cancer cells that inactivate the immune system, or inhibits T cell surface proteins (e.g., PD-1, etc.) or cytotoxic T-lymphocyte antigen (cytotoxic T-lymphocyte associated protein 4) (e.g., CTLA-4, etc.) to activate the T cells. Specifically, the antibody may include one or more selected from the group consisting of an anti-PD-L1 antibody, a derivative thereof, or an antigen-binding fragment thereof; anti-CTLA4 antibody, derivatives thereof or antigen-binding fragments thereof; anti-LAG-3 antibody, derivatives thereof or antigen-binding fragments thereof, anti-OX40 antibody, derivatives thereof or antigen-binding fragments thereof; anti-TIM3 antibody, derivatives thereof or antigen-binding fragments thereof; and anti-PD-1 antibody, derivatives thereof or antigen-binding fragments thereof. In one embodiment of the present disclosure, the PD-L1 antibody may be used. However, the present disclosure is not limited thereto.

In another example, the technical feature of the immunotherapy composition (e.g., imuGlue) according to the present disclosure is that the immunotherapy composition is prepared by combining the antibody to the mussel adhesive protein having a peptide cleavable by the MMP2 conjugated thereto regardless of the type of antibody. Therefore, it is obvious to those skilled in the art that the immunotherapy composition according to the present disclosure may separate and release antibodies therefrom in an intracellular environment, preferably a tumor microenvironment, and thus may be usefully utilized as a bio-responsive adhesive antibody delivery platform technology.

According to the present disclosure, the composition is characterized in that when exposed to MMP2, the peptide cleavable by the MMP2 in the bio-responsive adhesive antibody delivery platform according to the present disclosure is cleaved, thereby separating and releasing the antibody therefrom.

According to the present disclosure, the composition may be a spray or injection composition, but is not limited thereto. In one embodiment of the present disclosure, tumor growth is significantly inhibited when the imuGlue according to the present disclosure is sprayed on the primary tumor surgical resection site as a surgical attempt to remove most of the tumor. Furthermore, it was identified that the anti-tumor effect may be substantially improved to effectively reduce cancer recurrence. Further, it was identified that the imuGlue exhibits an enhanced anti-tumor effect even when the imuGlue is applied as an intratumoral injection without surgical operation, and thus the imuGlue may be usefully used in the treatment of cancer that is difficult to be subjected to surgical operation.

Further, the present disclosure provides a pharmaceutical composition for the prevention or treatment of cancer, the composition containing the immunotherapy composition according to the present disclosure.

According to the present disclosure, the cancer may include at least one selected from a group consisting of skin cancer, melanoma, gastric cancer, esophageal cancer, colon cancer, rectal colon cancer, pancreatic cancer, colorectal cancer, rectal cancer, bile duct cancer, liver cancer, brain tumor, leukemia, sarcoma, bone cancer, breast cancer, thyroid cancer, lung adenocarcinoma, uterine cancer, cervical cancer, endometrial cancer, prostate cancer, head and neck cancer, bladder cancer, endocrine cancer, urethral cancer, ovarian cancer, testicular cancer, kidney cancer, and lymphoma. However, it is not limited thereto.

According to the present disclosure, the pharmaceutical composition may be administered in combination with an IDO inhibitor (indoleamine (2,3)-dioxygenase inhibitor). The IDO inhibitor is a drug that inhibits an immunosuppressive factor in a tumor microenvironment and may be 1-MT (1-methyl-tryptophan), a D-isomer of 1-methyl-tryptophan, or NLG919, but is not limited thereto. In one embodiment of the present disclosure, 1-MT may be used as the IDO inhibitor, and thus it may be identified that the combination of imuGlue and 1-MT may effectively induce a T cell-mediated immune response.

According to the present disclosure, the pharmaceutical composition may be administered simultaneously with the IDO inhibitor, separately therefrom or sequentially therewith.

According to the present disclosure, the pharmaceutical composition may be in a form of a capsule, tablet, granule, injection, ointment, powder or beverage. The pharmaceutical composition may target a human being. The pharmaceutical composition may be formulated and used in the form of oral dosage forms such as powders, granules, capsules, tablets, aqueous suspensions, and form of external preparations, suppositories, and sterile injectable solutions, respectively, according to a conventional method. However, the present disclosure is not limited thereto.

The pharmaceutical composition according to the present disclosure may contain a pharmaceutically acceptable carrier. The pharmaceutically acceptable carrier may include a binder, a lubricant, a disintegrant, an excipient, a solubilizing agent, a dispersing agent, a stabilizing agent, a suspending agent, a pigment, a fragrance, etc. for oral administration. For injection, the pharmaceutically acceptable carrier may include buffers, preservatives, painless agents, solubilizers, isotonic agents, stabilizers, etc. in combination with each other. For topical administration, bases, excipients, lubricants, preservatives, etc. may be used as the pharmaceutically acceptable carrier. The formulation of the pharmaceutical composition according to the present disclosure may be variously prepared via mixing the composition with the pharmaceutically acceptable carrier as described above. For example, when administered orally, the formulation of the pharmaceutical composition may be prepared in the form of tablets, troches, capsules, elixirs, suspensions, syrups, wafers, etc. For an injection, the formulation of the pharmaceutical composition may be prepared in unit dosage ampoules or in multiple dosage forms.

In one example, examples of carriers, excipients and diluents suitable for the formulation may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate or mineral oil and the like. Further, fillers, anti-coagulants, lubricants, wetting agents, fragrances, emulsifiers, preservatives, etc. may be additionally contained therein.

The route of administration of the pharmaceutical composition according to the present disclosure may include oral, intravenous, intramuscular, intraarterial, intramedullary, intrathecal, intracardiac, transdermal, subcutaneous, intraperitoneal, intranasal, intestinal, topical, sublingual or rectal route. However, the present disclosure is not limited thereto. The "parenteral" administration may include subcutaneous, intradermal, intravenous, intramuscular, intraarticular, intra-synovial, intrastemal, intradural, intralesional and intracranial injection or infusion. The pharmaceutical composition according to the present disclosure may also be administered in the form of suppositories for rectal administration.

The dosage of the pharmaceutical composition according to the present disclosure may vary depending on various factors including the activity of the specific active component used, age, weight, general health, sex, diet, administration time, route of administration, release rate, drug combination and severity of specific disease to be prevented or treated. The dosage of the pharmaceutical composition varies depending on the patient's state, weight, disease severity, drug form, administration route and duration, but may be appropriately selected by those skilled in the art. Preferably, in consideration of all of the factors, an amount capable of obtaining a maximum effect in a minimal amount without side effects may be administered. More preferably, the composition may be administered repeatedly several times a day at an effective dose of 1 to 10000 µg/kg body weight/day, even more preferably 10 to 1000 mg/kg body weight/day. The dosage does not limit the scope of the present disclosure in any way.

Further, the present disclosure provides an anti-cancer adjuvant containing the immunotherapy composition according to the present disclosure.

According to the present disclosure, the term "anti-cancer adjuvant" means an agent that may improve, enhance or increase the anti-cancer effect of an anti-cancer agent. The anti-cancer adjuvant may be used as an anti-cancer agent or an anti-cancer adjuvant depending on the treatment concentration thereof and may enhance the sensitivity of anticancer drugs.

According to the present disclosure, the anti-cancer adjuvant may be administered in combination with a known compound having an effect of preventing, improving or treating cancer.

Further, the present disclosure provides a preparation method of a bio-responsive adhesive antibody delivery platform, the method including a step of covalently bonding the mussel adhesive protein to the C terminus of the peptide cleavable by MMP2 (matrix metalloproteinase-2).

Moreover, the present disclosure provides a method for preparing an immunotherapy composition, the method including covalently binding an antibody to an N terminus of a peptide cleavable by MMP2 (matrix metalloproteinase-2); and covalently binding a mussel adhesive protein to a C terminus of the MM2 cleavable peptide having the antibody binding thereto.

According to the present disclosure, the covalent bond may preferably be a linker mediated covalent bond.

The linker that mediates the covalent bond may be a linker (linker 1) that covalently bonds the N terminus of the peptide cleavable by MMP2 with the amine group (—$NH_2$) present in the antibody, or a linker (linker 2) that covalently bonds the C terminus of the peptide cleavable by MMP2 to the amine group (—$NH_2$) present in the mussel adhesive protein. The linkers 1 and 2 may be used without limitation.

In one embodiment of the present disclosure, Sulfo-SMCC may be used as the linker 1 and EDC and NHS may be used as the linker 2. Specifically, (1) in the "antibody-linker 1-peptide" combination, the amine group of the antibody and the thiol group (—SH) of the peptide cleavable by MMP2 may be reacted with Sulfo-SMCC such that they may be covalently bound to each other. Then, (2) EDC/NHS may be added thereto and reaction may occur for 30 minutes. Then, (3) the excess reagent may be removed using a Zeba spin desalting column. Then, (4) the mussel adhesive protein may be added thereto, and reaction may occur for 2 hours. Thus, in "peptide-linker 2-mussel adhesive protein" combination, the carboxyl group (—COOH) of the peptide may be covalently bonded to the amine group (—$NH_2$) of the mussel adhesive protein via EDC/NHS. Thus, the imuGlue according to the present disclosure may be prepared.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, the present disclosure will be described in detail based on an example. However, the following example is only to illustrate the present disclosure, and the present disclosure is not limited to the following example.

Experimental Materials and Methods

Cell Lines and Antibodies

MDA-MB-231 human breast cancer cells (ATCC No. HTB-26), luciferase/GFP double-labeled MDA-MB-231 cells (GeneCopoeia, Rockville, MD, USA) and B16-F10 mouse melanoma cells (ATCC No. CRL-6475) were incubated in Dulbecco's modified Eagle medium (DMEM; HyClone, UT, USA) supplemented with 10% (v/v) fetal bovine serum (FBS; HyClone) and 1% (v/v) penicillin/streptomycin. The cells were cultured in a humidified environment of 37° C. and 5% $CO_2$, and *mycoplasma* contamination was regularly identified.

Anti-human PD-L1 (clone 29E.2A3) and anti-mouse PD-L1 (clone 10F.9G2) antibodies were purchased from BioXCell (West Lebanon, N.H., USA). Alexa594-labeled anti-PD-L1 antibody was obtained from BioLegend (San Diego, Calif., USA). Anti-CD4 (clone RM4-5), anti-CD8 (clone 53-6.7), anti-Foxp3 (clone FJK-16) and anti-IFN-γ (clone XMG1.2) antibodies were purchased from BioLegend and eBioscience (San Diego, CA, USA). Alexa488-labeled Ab (anti-mouse IgG or anti-rabbit IgG) and DiO cell-labeled solution were purchased from Life Technologies (Grand Island, NY, USA).

Cytotoxicity Experiment

MAP was coated on polystyrene surfaces in various concentrations. MDA-MB-231 cells were seeded on each surface at a density of $5 \times 10^4$ cells per well and cultured for 24 hours. Subsequently, CCK-8 reagent (Dojindo Laboratories, Tokyo, Japan) was added to the cells on each surface and the cells were incubated for 3 hours. Cell viability was identified by measuring absorbance at 450 nm using a microplate absorbance spectrophotometer (PerkinElmer).

Confocal Microscopy Analysis

The bioactivity of Ab released from imuGlue was observed using a 24-well transwell plate with a 0.45 μm pore filter. MAP conjugated to Alexa594-labeled aPD-L1 was sprayed into an upper compartment of the transwell plate, and MDA-MB 231 or B16F10 cells ($2 \times 10^5$ cells per well) were seeded in a lower compartment thereof. After incubation for 24 hours in PBS containing 10 μg/ml MMP2 or in PBS, cell images were obtained using a confocal microscope (FLUOVIEW FV3000; IX83; Olympus) equipped with a 60×/1.35 immersion oil objective (Olympus).

For tumor section imaging analysis, tumor tissue was excised at end of the experiment and the excised tissue was fixed using 10% formalin (Sigma-Aldrich). Samples were frozen, and sectioned and mounted on glass slides. After rehydration of the section with PBS, the antigen was recovered via boiling in citric acid buffer (pH 6.0) before blocking with 1% BSA. Thereafter, the sections were incubated together with primary antibodies against CD4 and CD8 at room temperature for 1 hour. A fluorescently labeled secondary antibody was added thereto. Analysis was done using a confocal microscope.

Flow Cytometry

Dead cells were excluded via FVD (Fixable viability dyes; eBioscience) staining. For surface staining, cells were stained with fluorescence-labeled anti-CD4 and anti-CD8 antibodies. For intracellular staining, cells surface-stained using a Foxp3 staining kit (eBioscience) were fixed and permeated and stained with anti-Foxp3 and anti-IFN-γ antibodies. For intracellular cytokine staining, cells were stimulated for 6 hours with phorbol myristate acetate (PMA) and ionomycin in the presence of Golgi-Plug (BD Biosciences, San Jose, CA, USA) or Golgi-Stop (BD Biosciences). Data from the stained cells were collected using a flow cytometer (LSR Fortessa; BD Biosciences) equipped with 5 lasers and analyzed with FlowJo software (Treestar, Ashland, OR, USA).

Example 1. Preparation of imuGlue According to Present Disclosure 1-1. Preparation of imuGlue To prepare a bio-responsive adhesive antibody delivery platform to improve the retention time of aPD-L1 in a tumor microenvironment, and to provide optimal antibody release, the present inventors have covalently conjugated the bioengineered MAP to the antibody (aPD-L1) via a peptide linker that is cleavable by MMP2 (matrix metalloproteinase-2). The antibody and the antibody delivery platform having the antibody conjugated thereto were named "imuGlue". The imuGlue releases an antibody (aPD-L1) when exposed to MMP2 present in a tumor microenvironment.

First, the bioengineered MAP (Mussel Adhesive Protein) was produced in the *Escherichia coli* system as reported in Hwang, D. S. et al (2007). To convert the tyrosine residue of the bioengineered MAP to DOPA, the MAP was dissolved in a modified buffer (100 mM disodium phosphate, 20 mM boric acid and 25 ml ascorbic acid; pH 6.8) at a final concentration of 1.5 mg/ml. The MAP together with mushroom tyrosinase (100 μg/ml; Sigma-Aldrich, St. Louis, MO, USA) were cultured for 1 hour. Then, dialysis was performed in 1% (v/v) acetic acid. Hydrolysis in 6N HCl with 5% water-saturated phenol at 156° C. and then amino acid composition analysis were performed. Thus, a yield of MAP modified with DOPA was determined using an amino acid analyzer (S4300; SYKAM, Eresing, Germany). MAP in which tyrosine residues were converted to DOPA at high efficiency was used in the experiment.

The imuGlue was prepared by conjugating MAP to the Ab (aPD-L1 or Alexa488-labeled Ab) via a covalent bond using a peptide linker CGPLGVRGG (SEQ ID NO: 12, Peptron, Daejeon, Korea) that is cleavable by MMP2. Specifically, after diluting Ab in PBS (pH 7.4) to a final concentration of 1 mg/ml, 0.3 mg of Sulfo-SMCC (sulfosuccinimidyl-4-(N-maleimidomethyl)-cyclohexane-1-carboxylate; TCI Chemicals, Tokyo, Japan) in 30 μl DMSO was added to 1 ml of Ab and the mixture was stirred at room temperature for 30 minutes. Then, a peptide (0.25 mg) cleavable by MMP2 was added to the mixture with stirring at room temperature for 1 hour. The produced mixture was further incubated for 30 minutes together with 6 μM of EDC (1-ethyl-3-(3-dimethylaminopropyl)carbodiimide; Sigma-Aldrich) and 12 μM of NHS (N-hydroxysuccinimide; Sigma-Aldrich).

Excess reagent was removed via buffer exchange with 100 mM MES (2-(N-morpholino) ethanesulfonic acid) buffer with 0.5M NaCl at pH 6.5 using a Zeba spin desalting column (Thermo Fisher Scientific, Waltham, MA, USA). Next, the reaction mixture was incubated together with 7 mg MAP in 100 mM MES buffer using 0.5 M NaCl for 2 hours at room temperature, and pH 6.5.

1-2. Identification of Presence of MAP-Ab Conjugation of Prepared imuGlue

To visualize the MAP-Ab conjugate, MAP was labeled with Texas Red-X, succinimidyl ester (Life Technologies). The produced Texas Red-labeled MAP was further conjugated to Alexa488-labeled Ab as described above. After spraying the MAP-Ab conjugate on a glass slide, rinsing with PBS removed the unbound MAP-Ab. Thereafter, the glass slide was imaged using an in vivo fluorescence imaging system (Neoscience, Gyeonggi, Korea). The results are shown in FIG. 1.

As shown in FIG. 1, green and red "ImuGlue" indicate Ab labeled with Alexa488 and MAP labeled with Texas Red, respectively. The MAP-Ab conjugate was expressed in yellow color as an overlapping signal on the merged image, thus indicating that the MAP-Ab conjugate was stably obtained (scale bar=50 μm).

Further, in order to evaluate the conjugation ratio of MAP to Ab in the prepared imuGlue, MAP was conjugated to Alexa488-labeled Ab, and then dialyzed using a dialysis membrane with a molecular weight cuff-off (MWC) of 50 kDa. Thus, unreacted MAP was removed. Then, the Ab concentration was calculated by measuring Alexa-488 fluorescence using a fluorescence spectrometer (PerkinElmer, Waltham, MA, USA) at an excitation wavelength of 488 nm and an emission wavelength of 525 nm. Then, the MAP concentration was determined by subtracting the Ab concentration from the total protein concentration of MAP-Ab as measured by the Bradford assay (Bio-Rad, Hercules, CA, USA). The results are shown in FIGS. 2A and 2B.

Figure 2A:
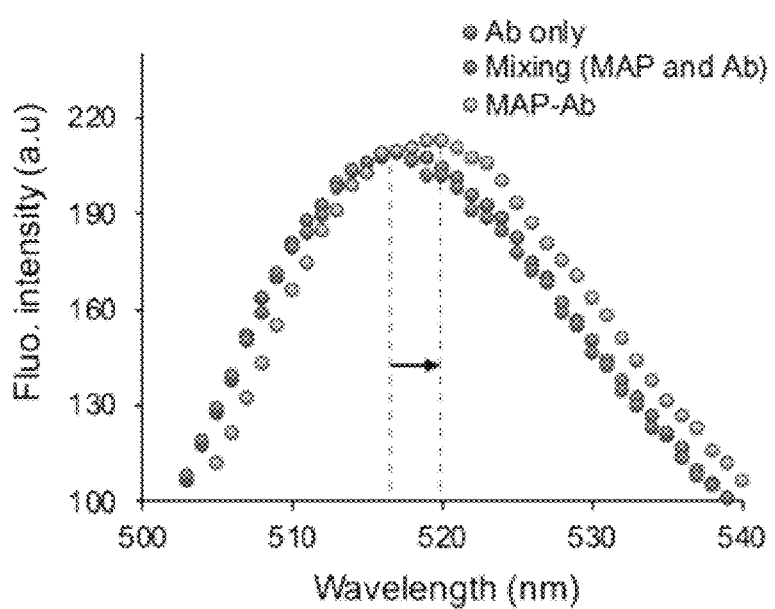
FIGS. 2A, 2B, 2C, 2D, 2E, and 2F are diagrams collectively showing the results of characterizing the imuGlue spray system according to the present disclosure.
Figure 2B:
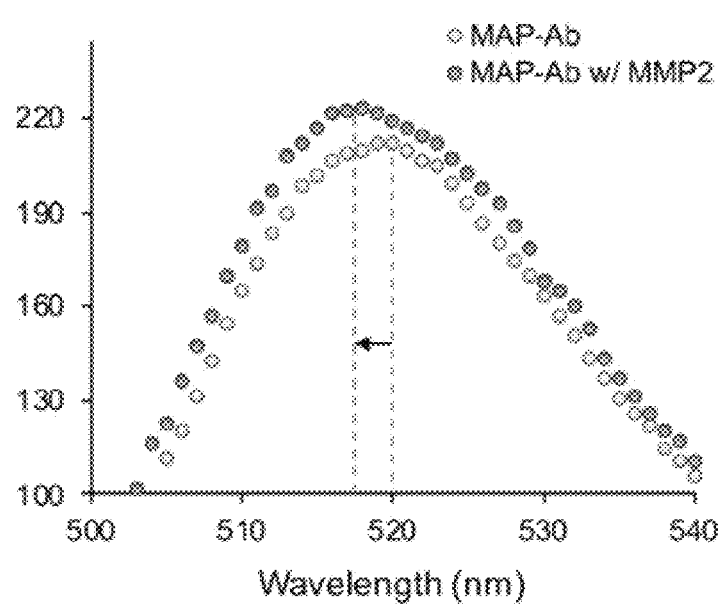

As shown in FIG. 2A, it was identified that a slight red shift (to 3 nm) in the emission spectrum of the MAP-Ab conjugate occurred compared to the free Ab and a simple mixture of MAP and Ab (FIG. 2A). This indicated that MAP and Ab were conjugated to each other. The red shift was presumed to be due to the molecular interaction between the fluorophore of Ab and the proximal phenol ring of MAP. Further, as shown in FIG. 2B, when MMP2 treatment was carried out, a blue shift was observed in the MAP-Ab emission spectrum. This shift was attributed to the increase in the distance between Ab and MAP due to cleavage of the peptide linker cleavable by MMP2. Further, it was identified based on the spectroscopic measurement of purified MAP-Ab that the average conjugation ratio based on the molar ratio of MAP to Ab is about 7.2.

Example 2. Surface Adhesion Force of imuGlue

DOPA is known to play a key role in surface adhesion and agglomeration of mussel byssus. Bioengineered MAP has been proven to have excellent underwater adhesion force due to DOPA (3,4-dihydroxyphenylalanine) as a main component thereof. In order to identify whether the imuGlue prepared in Example 1 had the MAP's unique underwater adhesion properties, the present inventors performed a QCM (quartz crystal microbalance) analysis to quantitatively measure the adhesion force of MAP-Ab during flow and compared the measured adhesion force of MAP-Ab with the adhesion force of free Ab.

Specifically, the resonance frequency of gold-coated quartz (8.9 MHz) was monitored using QCM (QCM922 A; Seikon EG&G, Tokyo, Japan) to evaluate the surface adhesion forces of MAP-Ab and Ab. To equilibrate the quartz crystal sensor, distilled water (DW) was injected into the QCM flow cell for 10 minutes. Thereafter, MAP-Ab or Ab (1 mg/ml) was injected into a flow module at a flow rate of 200 μl/min for 10 minutes until the frequency has been stabilized. The quartz crystal crystals were washed with distilled water to remove unattached Ab. Frequency shift values were measured in the whole process. The results are shown in FIG. 2C.

Figure 2C:
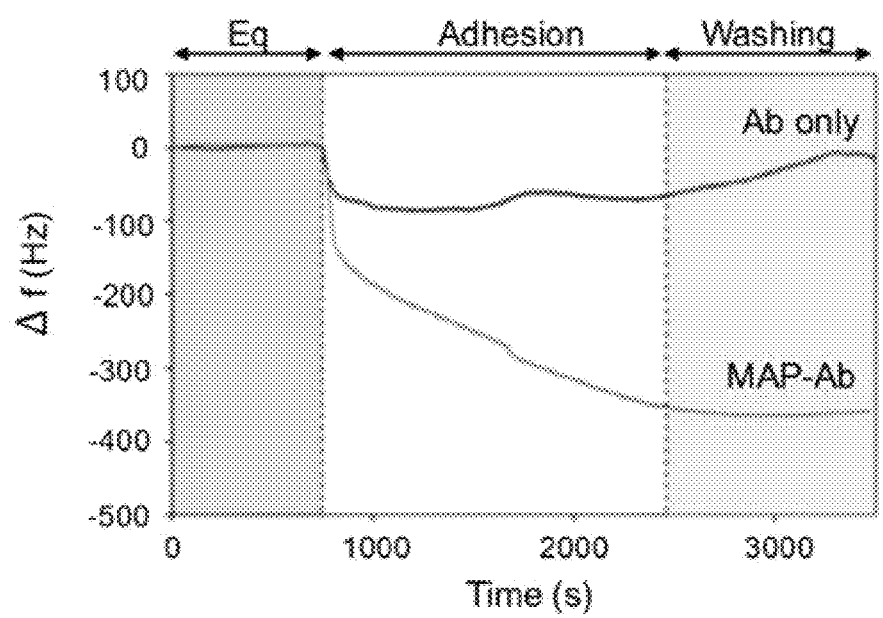

As shown in FIG. 2C, after the equilibration with distilled water, the resonance frequency change (Δf) of MAP-Ab at a flow rate of 200 μl/min was about 7 times higher than that of free Ab. This was maintained even during the washing step, thereby identifying that the MAP-Ab was stably attached to the quartz surface.

Further, as reported by Israelachvili, J. et al (2010), the underwater surface adhesion force of MAP-Ab was measured using the asymmetric mode of the Surface Force Apparatus (SFA) (SurForce LLC, Goleta, CA, USA). Specifically, the sample was coated on one side of the mica surface. Sample solutions (40 μg/ml in 0.1M MES, pH 6.5) were deposited on freshly cut mica surfaces and incubated for 10 minutes. The mica surface was rinsed using 0.1M MES buffer. The exposed mica surface and the coated mica surface were compressed for 5 minutes and held in 0.1M MES buffer for an additional 5 minutes. Thereafter, the mica surface was separated therefrom at a rate of 1 nanometer per second, which is the same rate as the compression rate. The surface adhesion was determined based on the separation distance immediately after the fracture. Further, the adhesion energy was calculated based on the Johnson-Kendall-Roberts adhesion theory. All experiments were performed multiple times independently for different contact points and mica surfaces. The results are shown in FIGS. 2D to 2E.

Figure 2D:
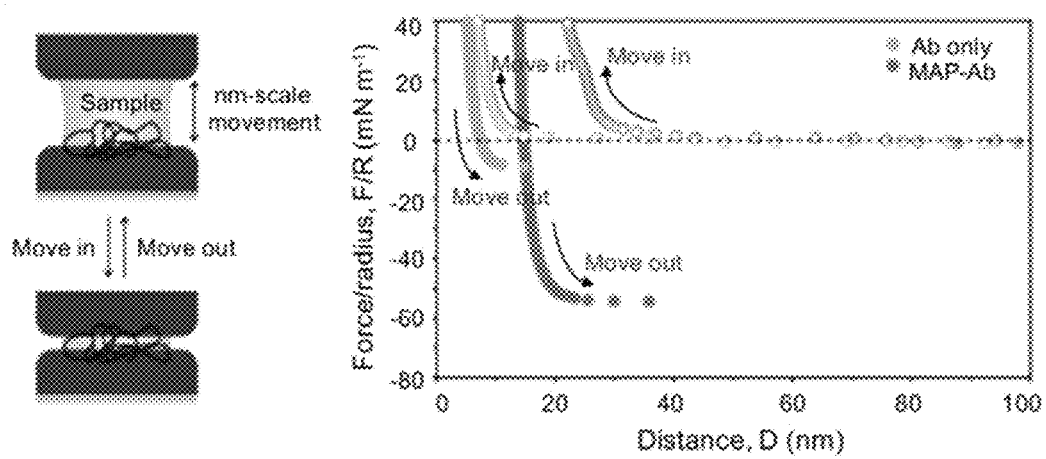
Figure 2E:
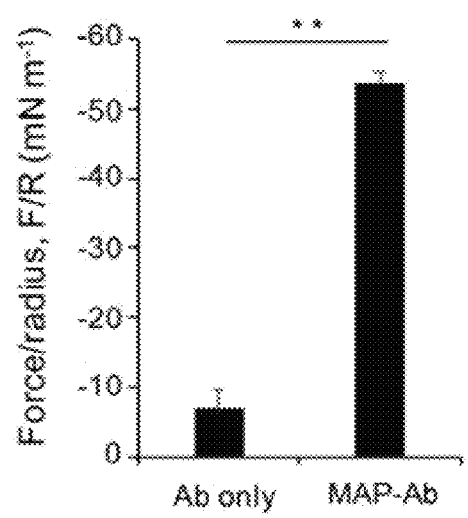

As shown in FIGS. 2D and 2E, the surface adhesion force of MAP-Ab (−53.68±1.76 mN/m) was about 8 times higher than that of free Ab (−6.82±2.84 mN/m). In another example, the surface adhesion force of MAP-Ab was similar to that previously reported for MAP46. The results indicated that the bonding of Ab had little effect on the MAP's unique underwater adhesion properties, and MAP-Ab had excellent underwater adhesion force due to MAP.

Example 3. Identification of Retention of imuGlue

The retention of imuGlue according to the present disclosure was identified using swine skin tissue (Stellen Medicine, St Paul, MN, USA) and glass slides. Specifically, one half of the swine skin tissue surface was covered with aluminum foil to prevent protein coating thereon. The other half thereof was sprayed with Alexa488-labeled MAP conjugated to Ab. The swine skin tissue surface was shaken and cultured for 24 hours in PBS at 37° C. After washing the swine skin tissue surface with PBS, the swine skin tissue surface was observed using a fluorescence microscope (BX60; Olympus, Tokyo, Japan).

In the same way, the adhesion force of Alexa488-labeled MAP conjugated to Ab onto the glass surface was examined. The MAP solution (7 mg/ml in 100 mM MES buffer) was sprayed onto a glass surface shielded with a mask having a hole in a shape of a letter "MAP". The MAP-sprayed surface was stained with Coomassie-Blue (Sigma-Aldrich) and shaken and cultured in PBS for 1, 3, 7, 14 days. The underwater adhesion properties of the MAP were analyzed using an optical microscope (Olympus). The results are shown in FIG. 2F, and FIG. 3

Figure 2F:
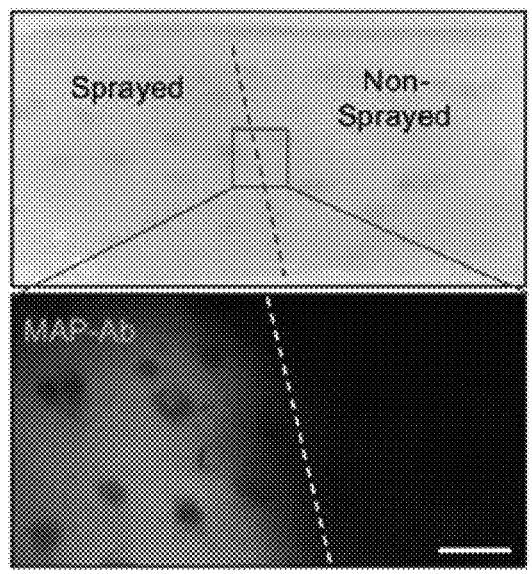
Figure 3A:
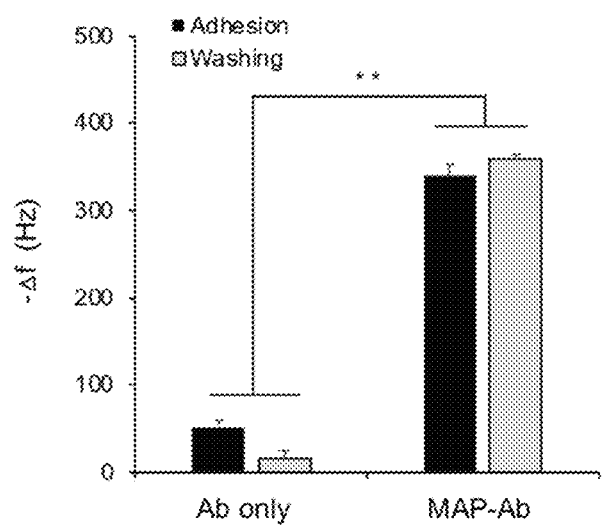
FIGS. 3A and 3B are diagrams collectively showing the results of identifying underwater adhesion force of the imuGlue according to the present disclosure.
Figure 3B:
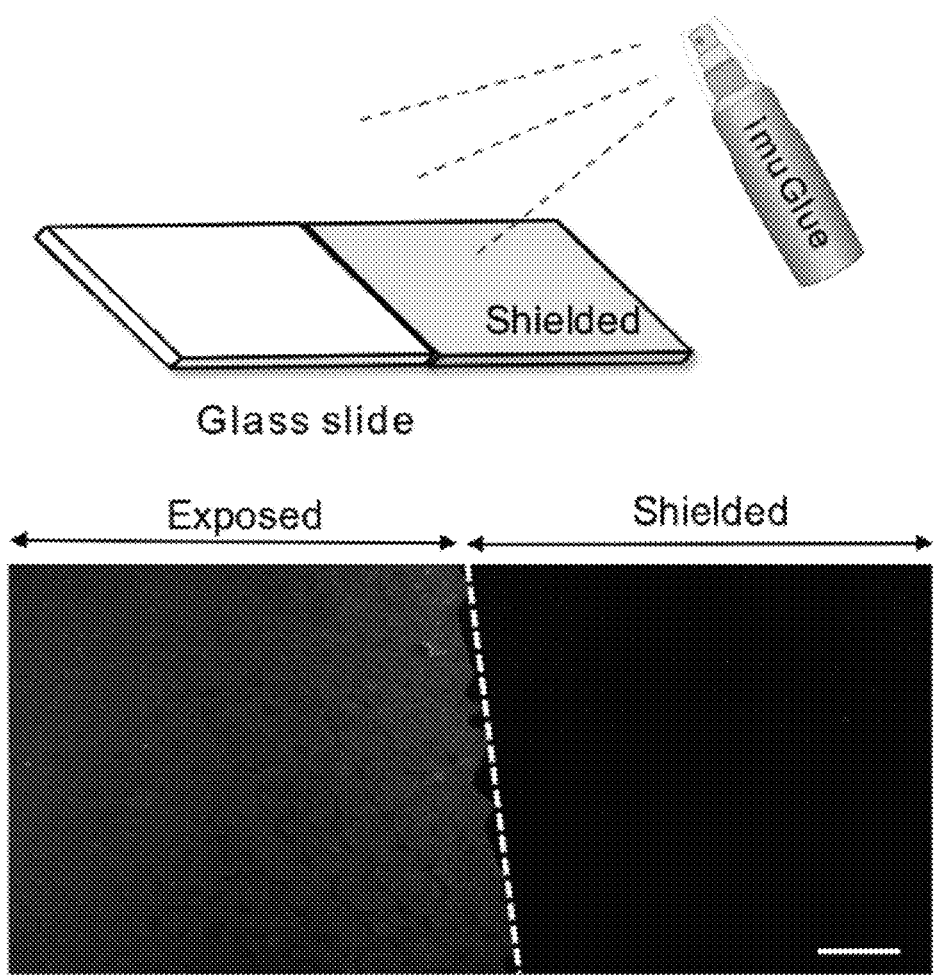

As shown in FIG. 2F and FIG. 3, it was identified that the unique adhesion force of MAP allowed the MAP-Ab sprayed on the swine skin tissue and the glass surface to be retained thereon for more than 2 weeks under underwater conditions.

Example 4. Identification of Environment-Responsive Release of ImGlue

In order to observe the Ab release profile of imuGlue upon exposure to MMP2, the Alexa488-labeled MAP-Ab was sprayed onto a 48-well plate and cultured in PBS or PBS containing 10 μg/ml MMP2 (Sino Biological, Wayne, PA, USA) at 37° C. Supernatants containing the released Ab were collected and quantified by measuring Alexa488 fluorescence. Further, the Alexa488-labeled MAP conjugated to Ab was sprayed on a glass surface, and incubated for 7 days, and then 10 μg/ml MMP2 was added thereto. The release of Ab was visualized using a fluorescence microscope. The results are shown in FIG. 4.

Figure 4A:
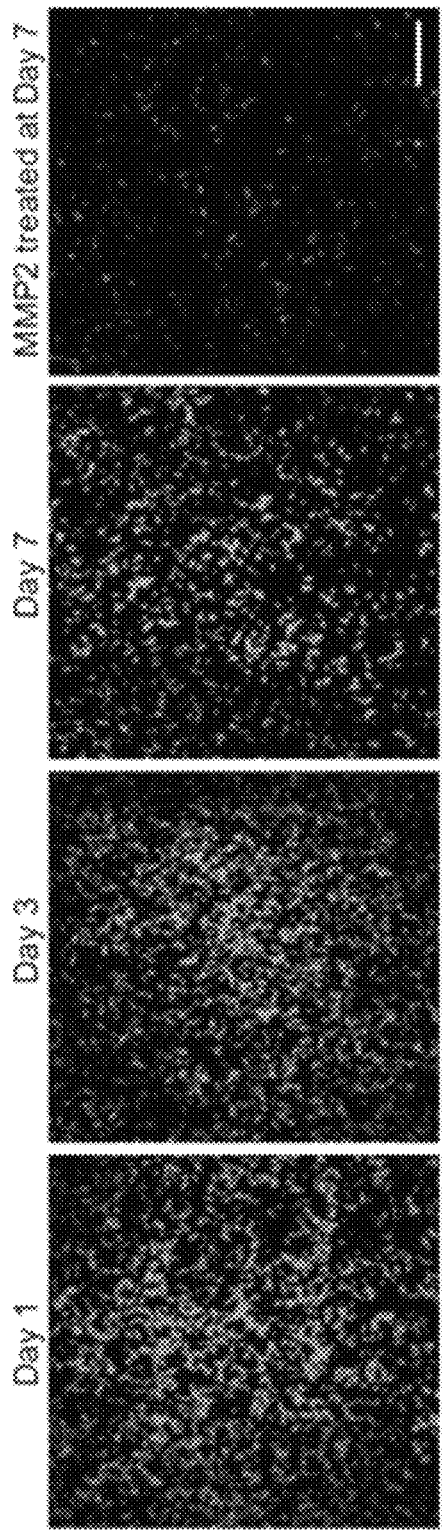
FIGS. 4A and 4B collectively show the release profile of MMP2-responsive Ab.
Figure 4B:
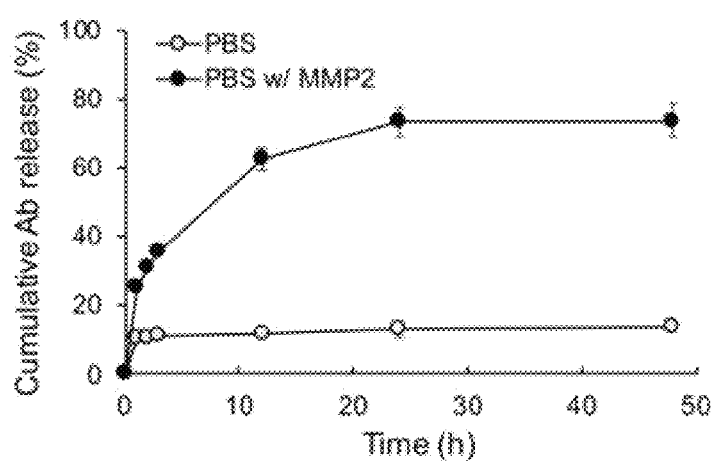

As shown in FIG. 4A, it was identified that MAP-Ab sprayed on the glass surface remained stable under underwater conditions for 7 days, whereas MMP2 treatment on the surface on the 7th day caused Ab release. Further, as shown in FIG. 4B, the cumulative Ab release profile suggested that the imuGlue may release 75% of Ab sprayed for 24 hours in the presence of MMP2.

It was identified based on the above results that when the imuGlue according to the present disclosure responds to the tumor microenvironment, that is, is exposed to MMP2, Ab is efficiently in situ released from the MAP-Ab and thus the imuGlue has an environment responsiveness.

Example 5. Identification of Effect of imuGlue In Vivo Using Cancer Animal Model 5-1. Observation of Ab Retention In Vivo All animal studies were carried out with the approval of the Animal Care Agency and the POSTECH Use Committee (POSTECH IACUC-2016-0044-R2). In order to identify whether the imuGlue according to the present disclosure may enhance the in vivo retention time of Ab, the retention of Ab was evaluated by injecting the Alexa488-labeled MAP conjugated to Ab into a cancer animal model.

Specifically, Alexa488-labeled Ab or Alexa488-labeled MAP conjugated to the free Ab was injected subcutaneously, at the same dose as Ab (1 mg/kg), into a right flank of BALB/c nude mice. Fluorescence images were acquired using an in vivo imaging system with an exposure time of 1 second to observe Ab retention in vivo. The average of the integrated density (area×strength unit) was determined via quantification of a region of interest using the imaging software NEOimage (Neoscience). Further, blood was collected from mice in 6 and 24 hours after the subcutaneous injection of the Alexa488-labeled MAP conjugated to Ab or the Alexa488-labeled Ab. Plasma was obtained by centrifuging the sample at 14,000×g for 10 minutes. Ab concentration was calculated by measuring Alexa488 fluorescence using a fluorescence spectrometer. The results are shown in FIGS. 5A to 5C.

Figure 5A:
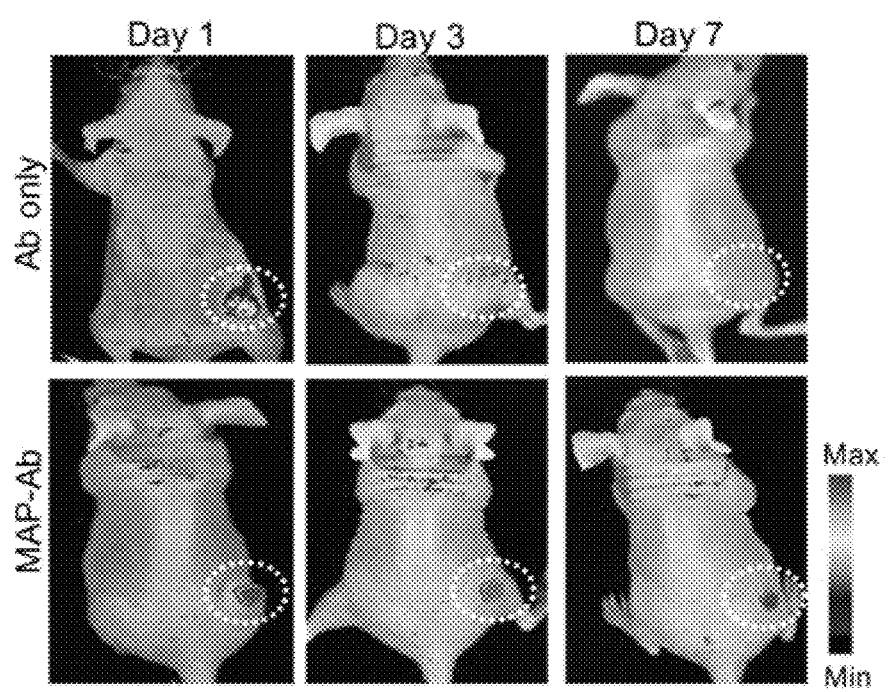
FIGS. 5A, 5B, 5C, 5D and 5E are diagrams collectively showing the results of identifying enhanced antibody retention in vivo when using the imuGlue according to the present disclosure.
Figure 5B:
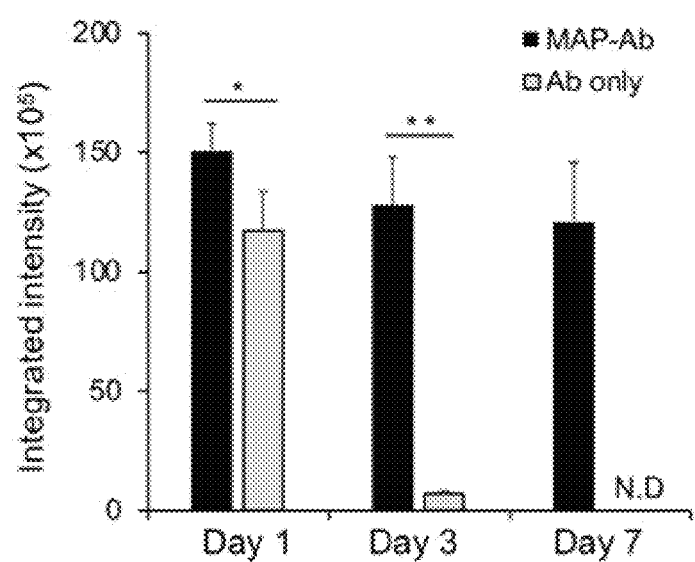
Figure 5C:
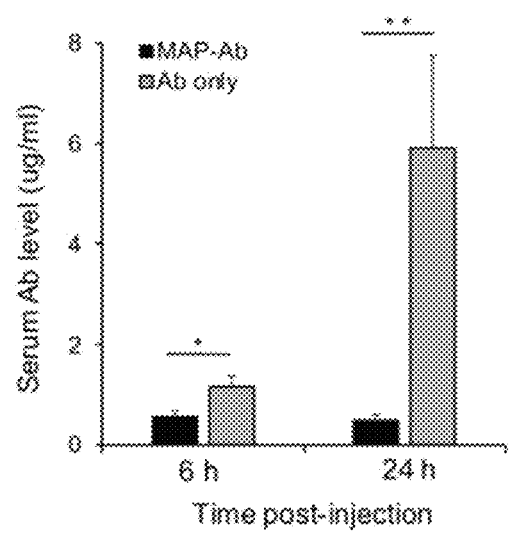

As shown in FIGS. 5A and 5B, it was identified that MAP-Ab maintained Ab in vivo for a period of 1 week or longer without significant loss thereof, while the free Ab was hardly detected on the 3rd day after the injection. Further, it was identified based on a result of measuring the Alexa488-labeled Ab levels in serum collected after the subcutaneous injection that the high level of circulating Ab was detected in serum within 24 hours after the injection of the free Ab, as shown in FIG. 5C. This suggested dissemination of Ab due to the systemic circulation. On the other hand, a negligible level of Ab was detected in serum at 6 and 24 hours after injection of the MAP-Ab. This means that the imuGlue significantly improves the retention time in vivo of Ab. It was identified based on the results that the imuGlue according to the present disclosure may effectively prevent extensive systemic exposure to the immune agent and further reduce off-target inflammatory symptoms.

Figure 5D:
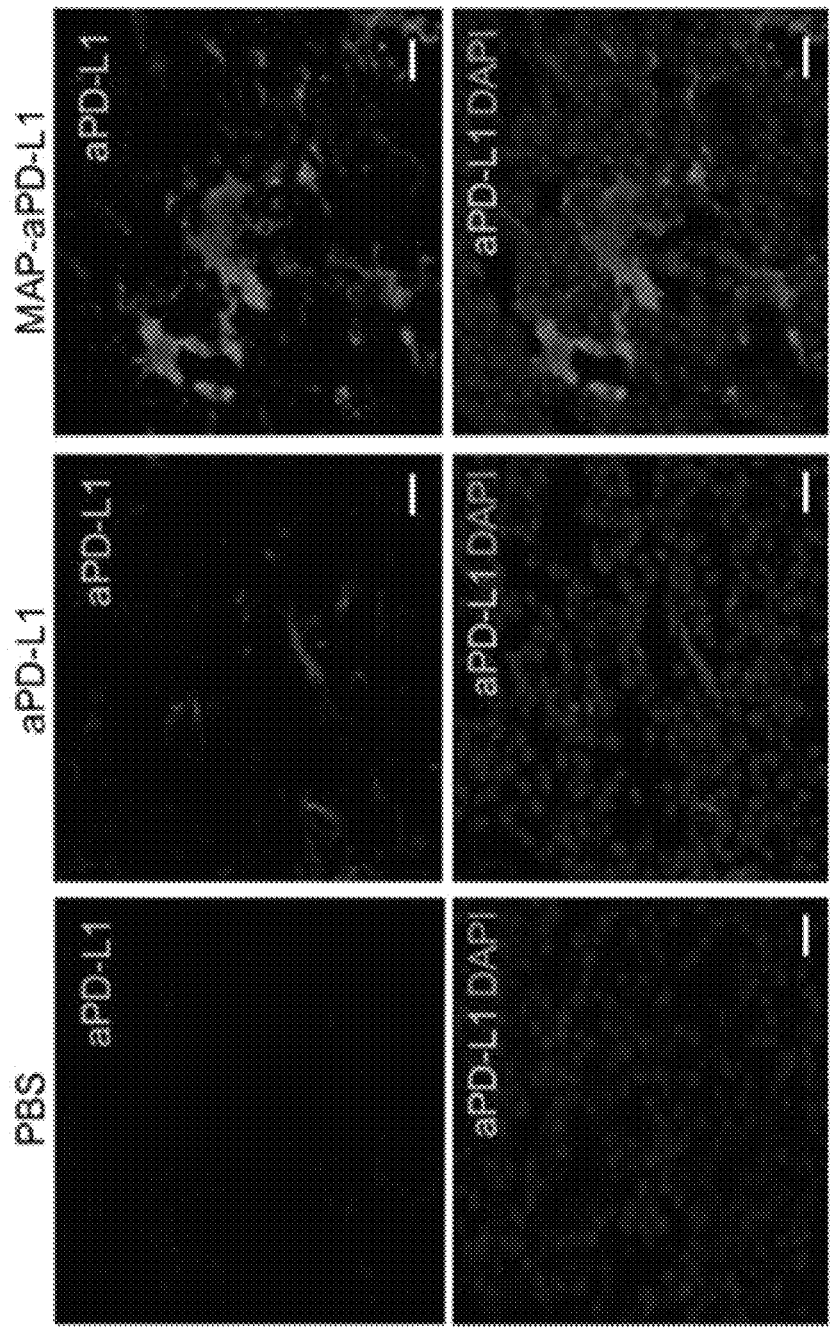

Furthermore, in order to identify whether the imuGlue according to the present disclosure may promote the preferential retention of the aPD-L1 against cancer in vivo, MAP conjugated to aPD-L1(MAP-aPD-L1) was additionally sprayed onto tumor tissue (about 200 mm³). On 7 days after the treatment, tumor tissue was collected, and immunofluorescence imaging thereof was performed to evaluate retention of aPD-L1. As a result, as shown in FIG. 5D, the confocal image of the tumor section indicated that the MAP-aPD-L1 treatment allowed the aPD-L1 retention time in the tumor microenvironment to be significantly increased, compared to the free aPD-L1 treatment. The results suggest that the aPD-L1 has the systemic circulation and thus is rapidly disseminated to other tissues when the free aPD-L1 is administered, while the retention time of the antibody at the tumor site is significantly enhanced when the free aPD-L1 is conjugated with MAP.

5-2. Evaluation of Activity of Released aPD-L1

Whether to enhance the retention time of aPD-L1 at the tumor site may be an important factor. Further, whether the bioactivity of aPD-L1 is maintained in the tumor microenvironment such that the released aPD-L1 effectively binds to the tumor's PD-L1 antigen to block the PD-L1/PD-1 signaling pathway may be the important factor. Thus, the bioactivity of the aPD-L1 released from the imuGlue in the presence of MMP2 was evaluated using a transwell system (FIG. 6A). The results are shown in FIG. 5E and FIG. 6B.

Figure 5E:
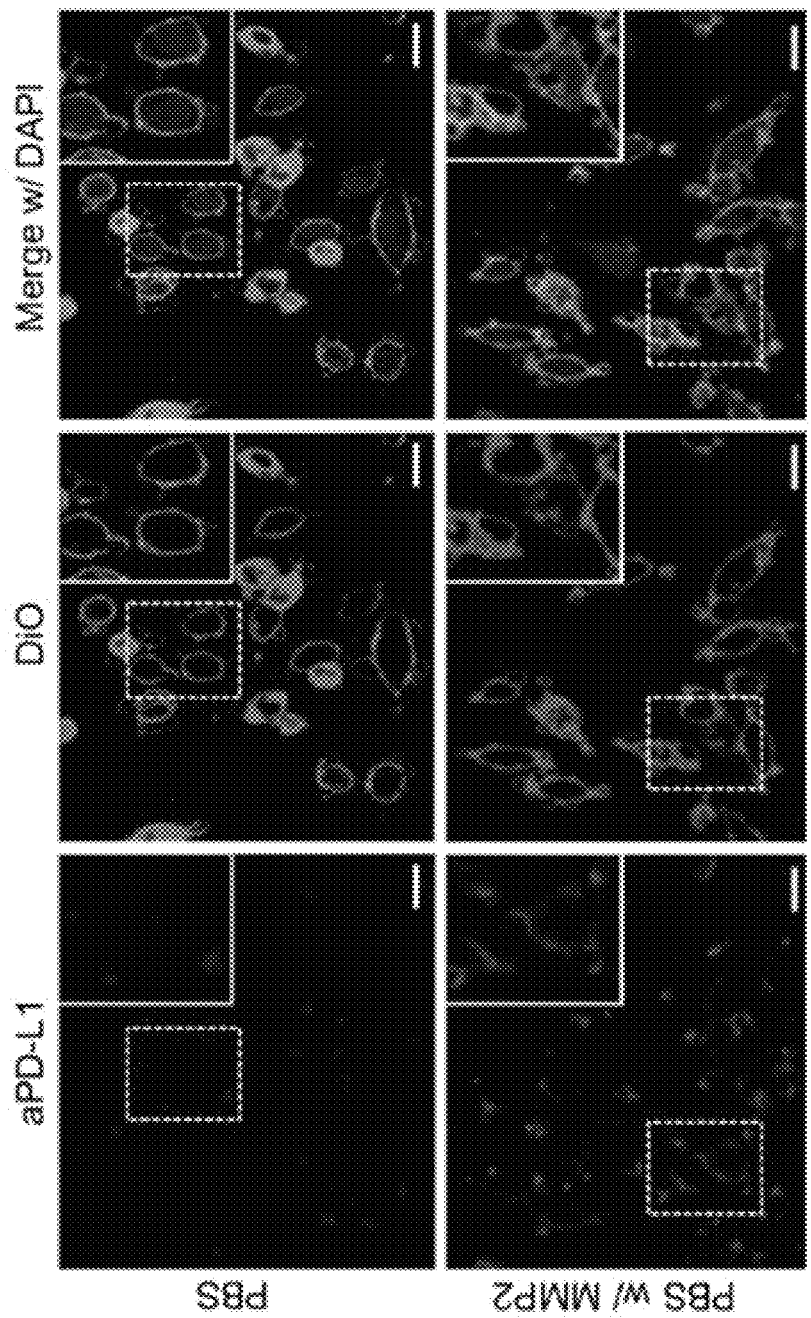
Figure 6A:
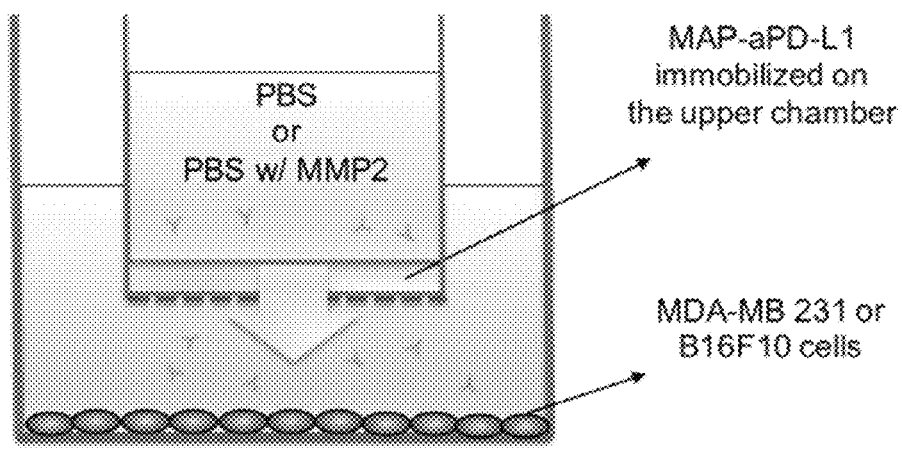
FIGS. 6A and 6B are diagrams collectively showing the results of identifying bioactivity retention of aPD-L1 released from imuGlue according to the present disclosure.
Figure 6B:
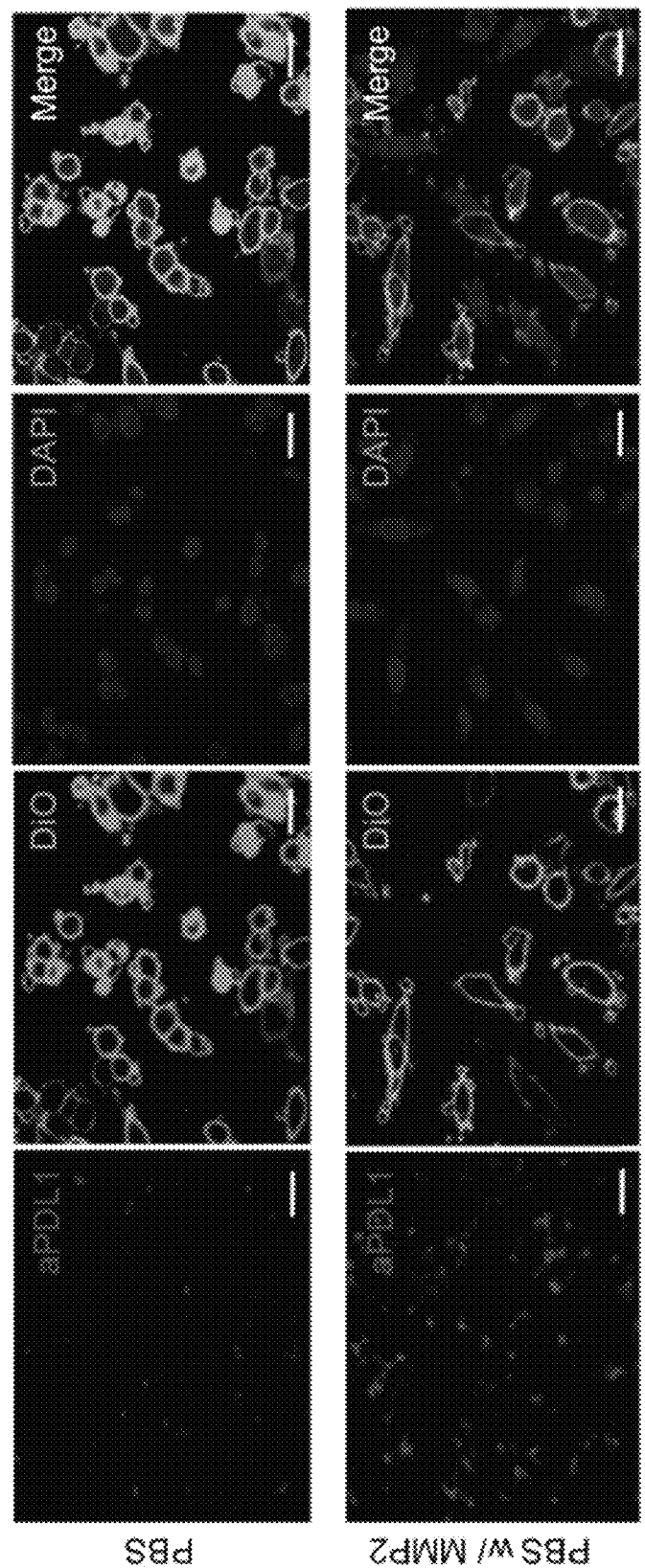

As shown in FIG. 5E and FIG. 6B, the released aPD-L1 successfully bound to cancer cells. Thus, it was identified that the aPD-L1 released from imuGlue due to the MMP2 maintains bioactivity. Based on the results, it was identified that the imuGlue platform according to the present disclosure not only improves the retention time of antibodies in vivo, but also promotes the release of bioactive therapeutic agents in a tumor microenvironment, as needed.

Example 6. Reduction of Cancer Growth Due to imuGlue Use

Figure 7A:
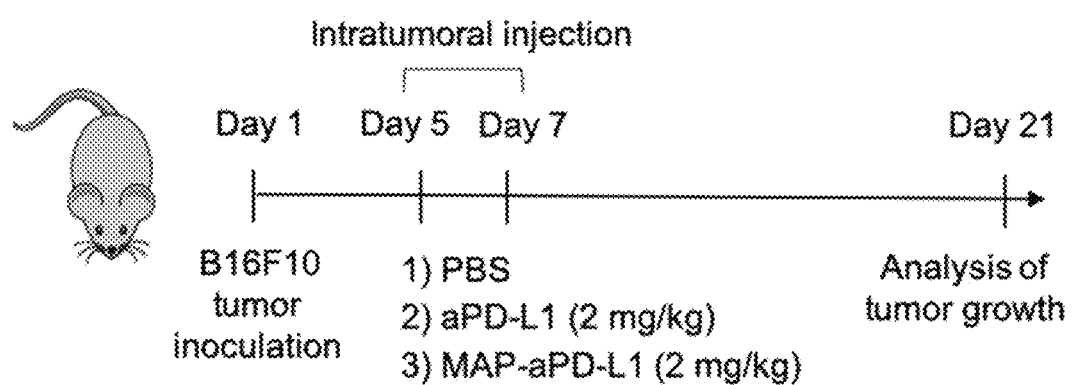
FIGS. 7A, 7B, 7C, 7D, 7E and 7F are diagrams collectively showing reduced in vivo tumor growth by using imuGlue.

To further identify whether the imuGlue according to the present disclosure may reduce tumor growth in vivo, the present inventors employed the highly aggressive B16F10 melanoma model and administered imuGlue via intratumoral injection (FIG. 7A). Specifically, female BALB/c C57BL/6 mice (6 to 10 weeks old) were purchased from OrientBio (Seongnam, Korea). A tumor xenograft model was prepared by subcutaneously injecting $1\times10^7$ B16F10 melanoma cells into the right flank of C57BL/6 mice. The melanoma-bearing mice were randomly divided into 3 groups (n=6) which in turn were anesthetized with isoflurane when the tumor volume reached approximately 100 mm$^3$. The mice were treated with PBS, aPD-L1, or MAP-aPD-L1 at 2 mg/kg aPD-L1 by intratumor injection twice on day 5 and 7. A tumor volume was estimated by measuring a tumor size using an electronic caliper and then calculating the tumor volume based on the tumor size using a formula: area$^2\times$length$\times 0.5$. A survival rate was represented by a Kaplan-Meier curve. The survival end point was determined as a time when the tumor volume reached 1,000 mm$^3$.

Figure 7B:
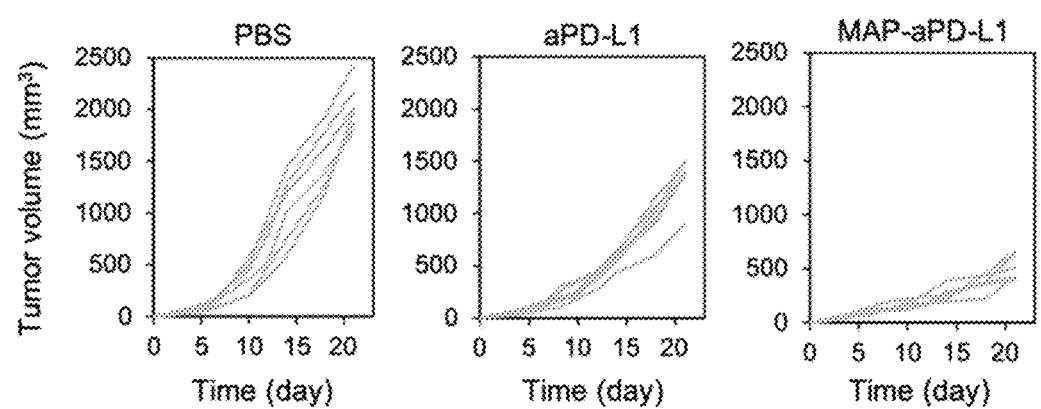
Figure 7C:
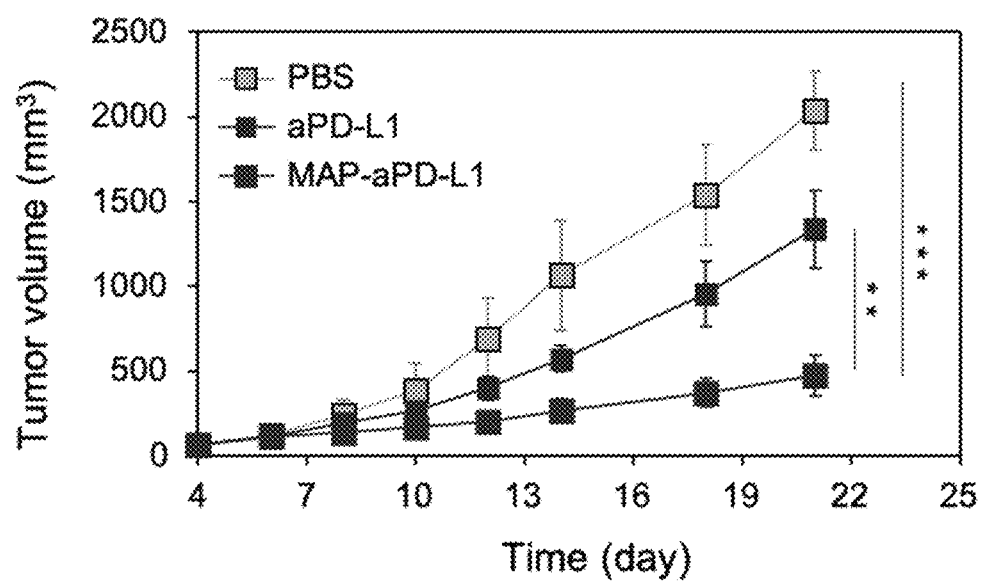
Figure 7D:
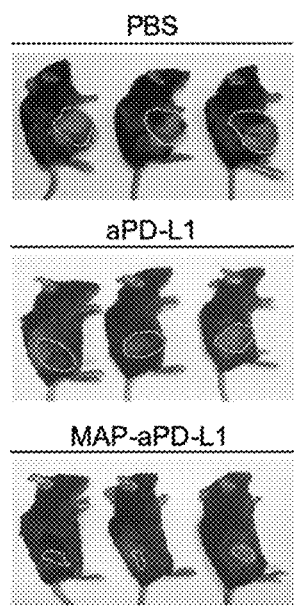
Figure 7E:
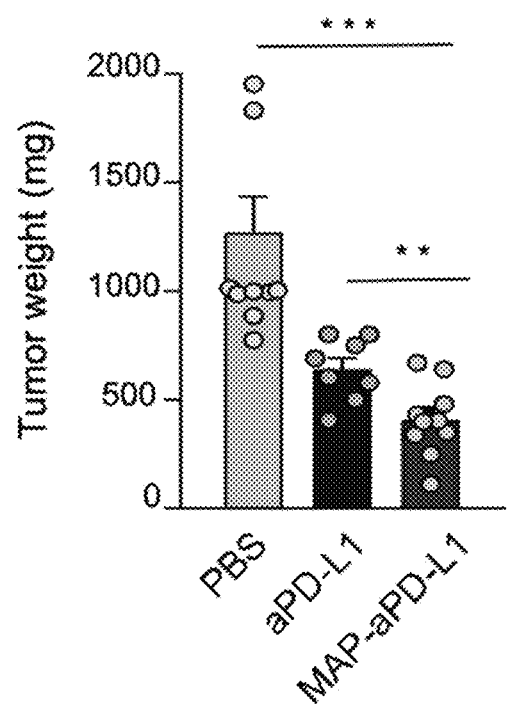
Figure 7F:
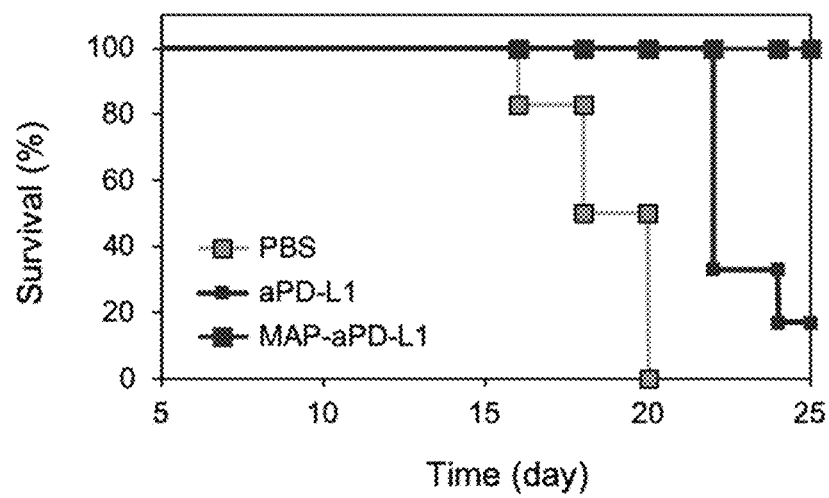

As a result, as shown in FIGS. 7B to 7F, the mice treated with MAP-aPD-L1 exhibited the significant suppression of tumor growth, whereas only slightly delayed tumor growth was observed in mice treated with free aPD-L1 (FIGS. 7B and 7C). Furthermore, the mice treated with MAP only showed no suppression of tumor growth compared to PBS treatment, demonstrating that the reduced tumor growth was primarily due to aPD-L1 anti-tumor activity. The end point analysis showed a protective effect against the tumor progression in MAP-aPD-L1-treated mice, as evidenced by the significantly reduced tumor size and weight compared to that in mice treated with PBS and free aPD-L1 (FIGS. 7D and 7E). In addition, the mouse survival rate, which corresponded to the tumor size, indicated robust protection from tumor growth in MAP-aPD-L1-treated mice, whereas none of the mice survived in the PBS treatment group, and a significantly lower survival rate (~20%) was observed in the free aPD-L1 treatment group within 25 days (FIG. 7F).

It was identified based on the results that the imuGlue according to the present disclosure enhances the retention time of the aPD-L1 at the tumor site and optimally releases the aPD-L1, thereby substantially improving the anti-tumor effect of immunotherapy after the surgery to prevent the cancer recurrence.

Example 7. Identifying Effect of imuGlue on T Cell-Mediated Anti-Tumor Immunity

Figure 8A:
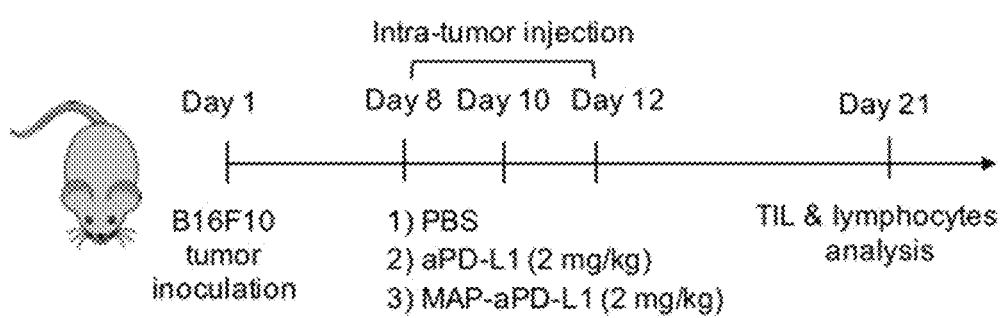
FIGS. 8A, 8B, 8C, 8D, 8E, 8F, 8G and 8H are diagrams collectively showing the results of identifying the T cell-mediated anti-tumor immune response of imuGlue according to the present disclosure.

The therapeutic limitation of aPD-L1 therapy may be due to insufficient lymphocyte infiltration, which plays an important role in cancer immunity. To investigate the effect of the imuGlue treatment on the invasion of immune cells into tumors, experiments were performed using a low immunogenicity B16F10 mouse melanoma model (FIG. 8A). Specifically, C57BL/6 mice were inoculated with B16F10 cancer cells subcutaneously and were randomly divided into 3 groups. Then, PBS, aPD-L1 or MAP-aPD-L1 were injected intratumorally thereto on the 8th, 10th and 12th days. The results are shown in FIGS. 8B to 8H.

Figure 8B:
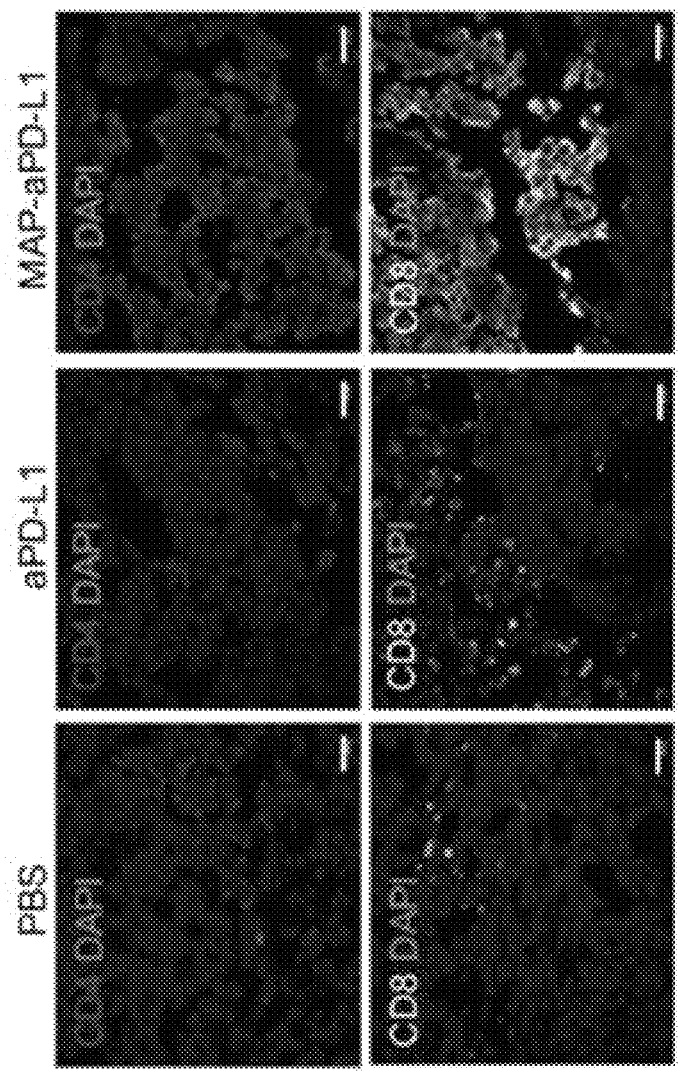
Figure 8C:
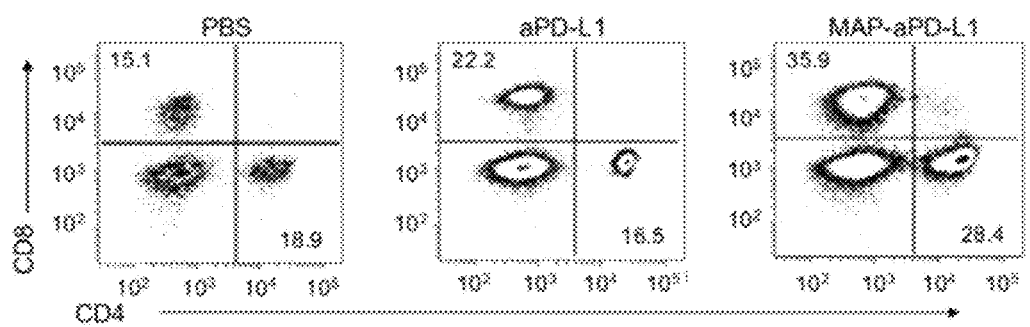
Figure 8D:
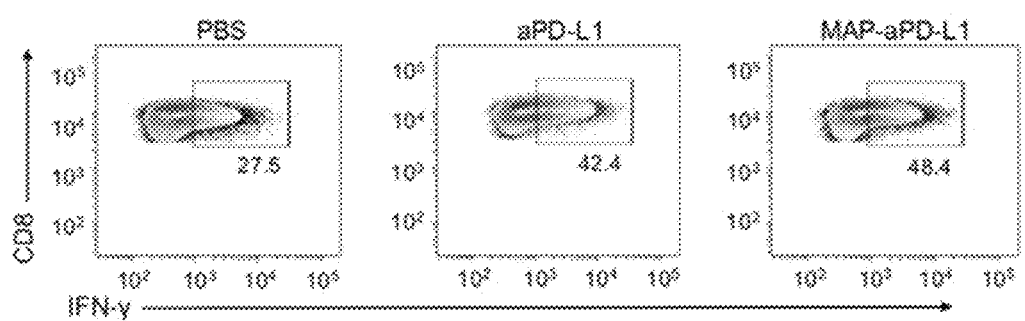
Figure 8E:
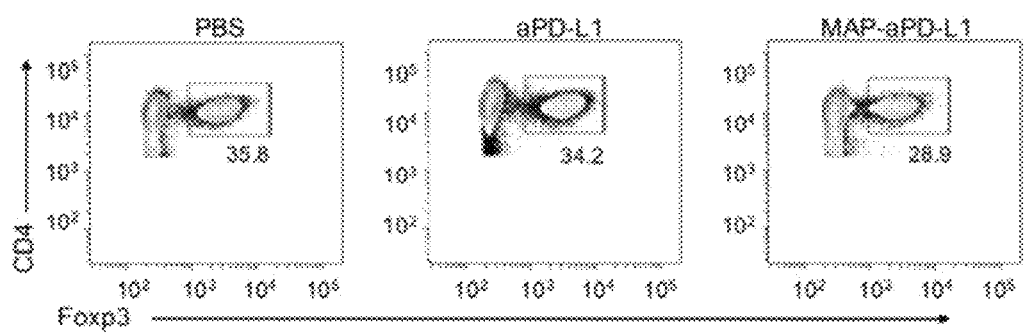
Figure 8F:
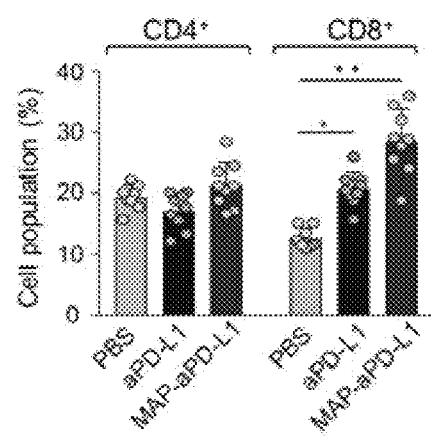
Figure 8G:
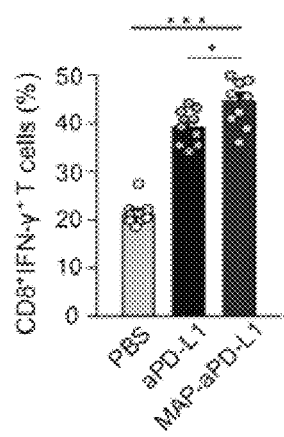
Figure 8H:
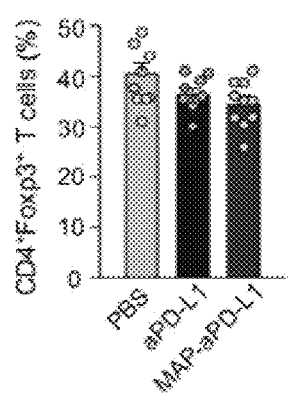

Further, as shown in FIG. 8B, the administration of MAP-aPD-L1 increases the infiltration of CD8+ and CD4+ T cells into the tumor, while T cell infiltration is restricted when the mice were treated with PBS or free aPD-L1. Furthermore, it was identified based on a result of further analysis of tumor infiltrating lymphocytes (TIL) collected from tumors in 9 days after the treatment using flow cytometry that the percentage of CD8+ T cells in tumors treated with MAP-aPD-L1 increased by 2 to 3 times, compared to that when the tumor was treated with PBS and free aPD-L1 (FIGS. 8C and 8F). CD8+TIL of the MAP-aPD-L1 treatment group significantly increased the production of IFN-γ, as an important effector cytokine of the anticancer immune response (FIGS. 8D and 8G). Although regulatory T cell (Treg) percentage of tumor infiltrating CD4+Foxp3+ regulatory T cells decreased, the increase in CD8+ and IFN-γ+ CD8+ T cells was observed in MAP-aPD-L1-treated tumors, thus resulting in an enhanced T cell-mediated anti-tumor immune response due to the imuGlue treatment (FIGS. 8E and 8H).

The above results indicate that the imuGlue according to the present disclosure effectively delivers aPD-L1 to the tumor microenvironment and enhance the T cell-mediated anti-tumor immunity to induce the significantly enhanced anti-tumor effect.

Example 8. Application of imuGlue to Combined Immunotherapy

To overcome the limitations of the low responsiveness to the single checkpoint inhibitor (ICI) drugs, combination therapies with therapeutic strategies such as chemotherapy, radiation therapy and other immunotherapies are widely used. Many of these combination strategies have been shown to improve anti-tumor effects, but the co-administration of these drugs has the problem of significantly increasing immune toxicity systemically. Thus, along with the treatment of aPD-L1 with imuGlue, the present inventors have evaluated the imuGlue as a topical combination therapy platform for effective delivery of multiple immunomodulatory drugs in combination with 1-MT (1-methyltryptophan) as an inhibitor of the immunosuppressive enzyme IDO (Indoleamine 2,3-dioxygenase) which is overexpressed in the tumors and dendritic cells and inhibits T cell proliferation and activation.

Figure 9A:
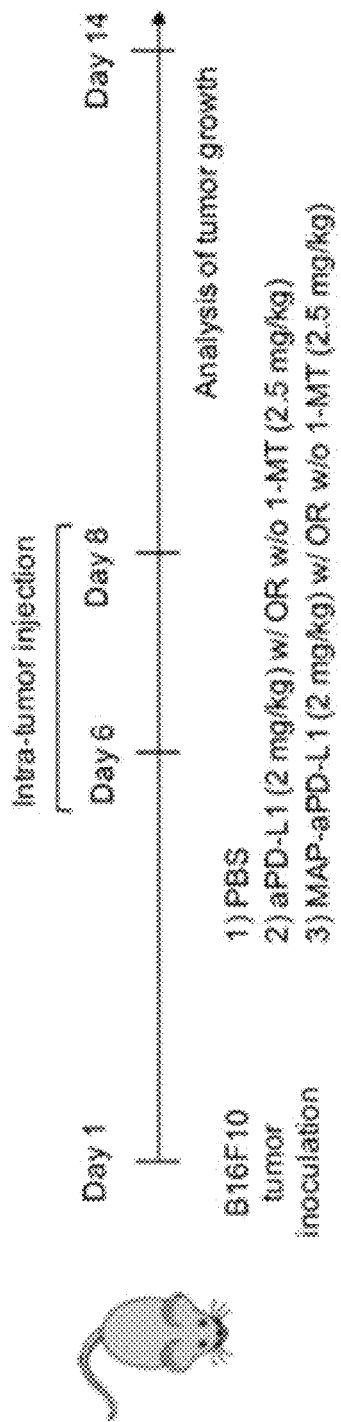
FIGS. 9A, 9B, 9C, 9D and 9E collectively show that the anti-tumor efficacy is enhanced by combination immunotherapy with an IDO-blocking agent.

First, for combined immunotherapy, an aggressive melanoma B16F10 melanoma model was established by subcutaneously injecting $1\times10^7$ B16F10 cells into the right flank of a BALB/c nude mouse without tumor resection (FIG. 9A). When the tumor volume reached approximately 100 mm$^3$, B16F10 tumor-bearing mice were randomly divided into 5 groups (n=6) and then imuGlue was injected intratumorally thereto. Specifically, on days 6 and 8, PBS, aPD-L1, and MAP-aPD-L1 of the same dose as that of aPD-L1 (2 mg/kg) in combination with 1-MT (2.5 mg/kg) were sequentially injected intratumorally to the mice, respectively.

Tumor growth and body weight were observed throughout the entire experiment. The results are shown in FIGS. 9B to 9E.

Figure 9B:
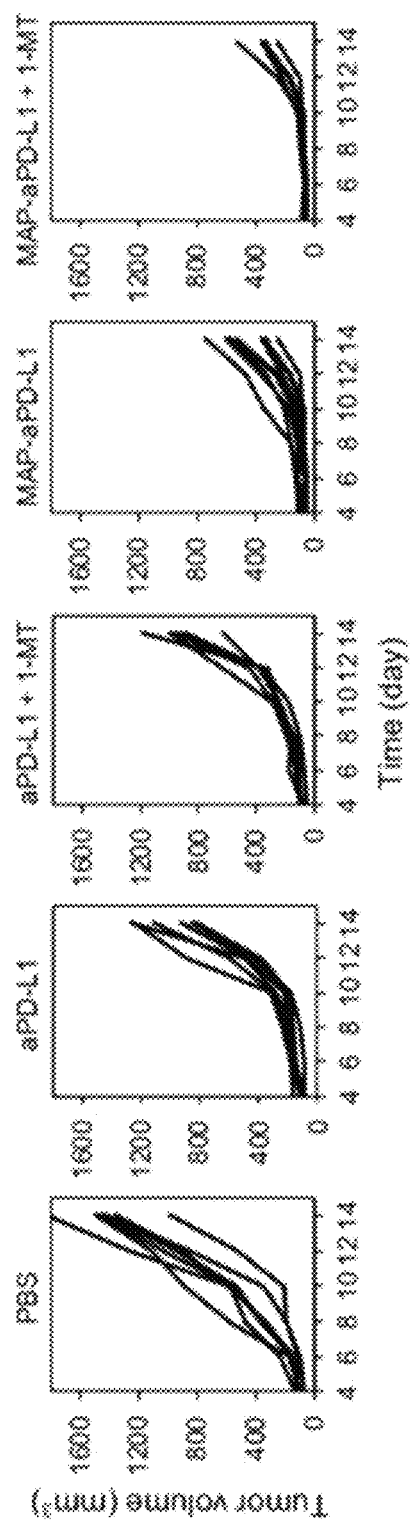
Figure 9C:
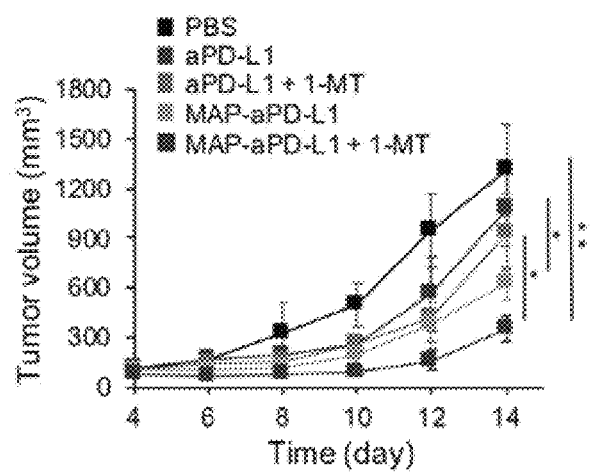
Figure 9D:
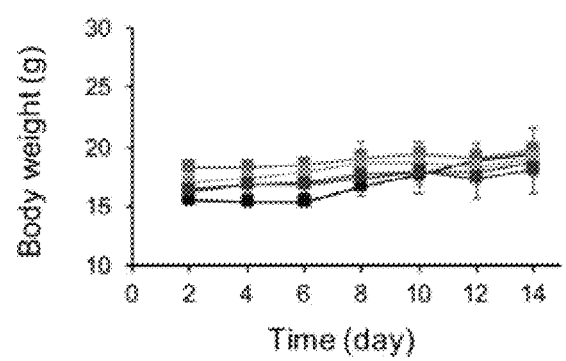
Figure 9E:
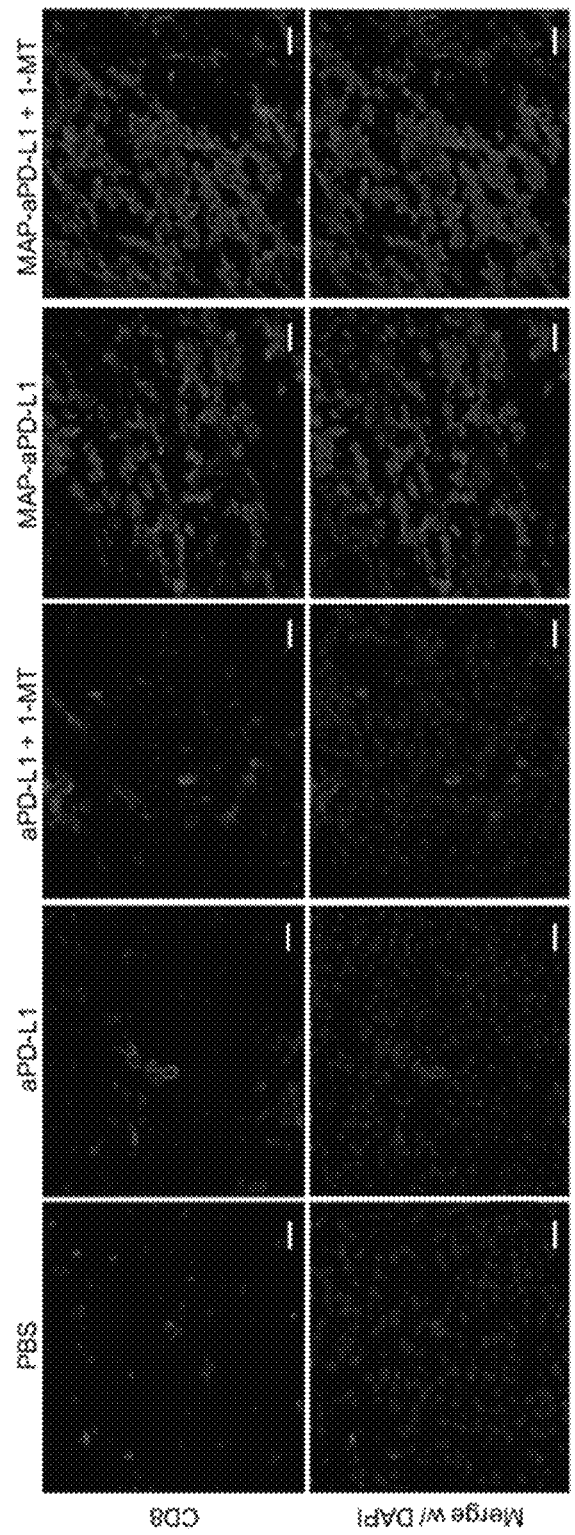
Figure 10:
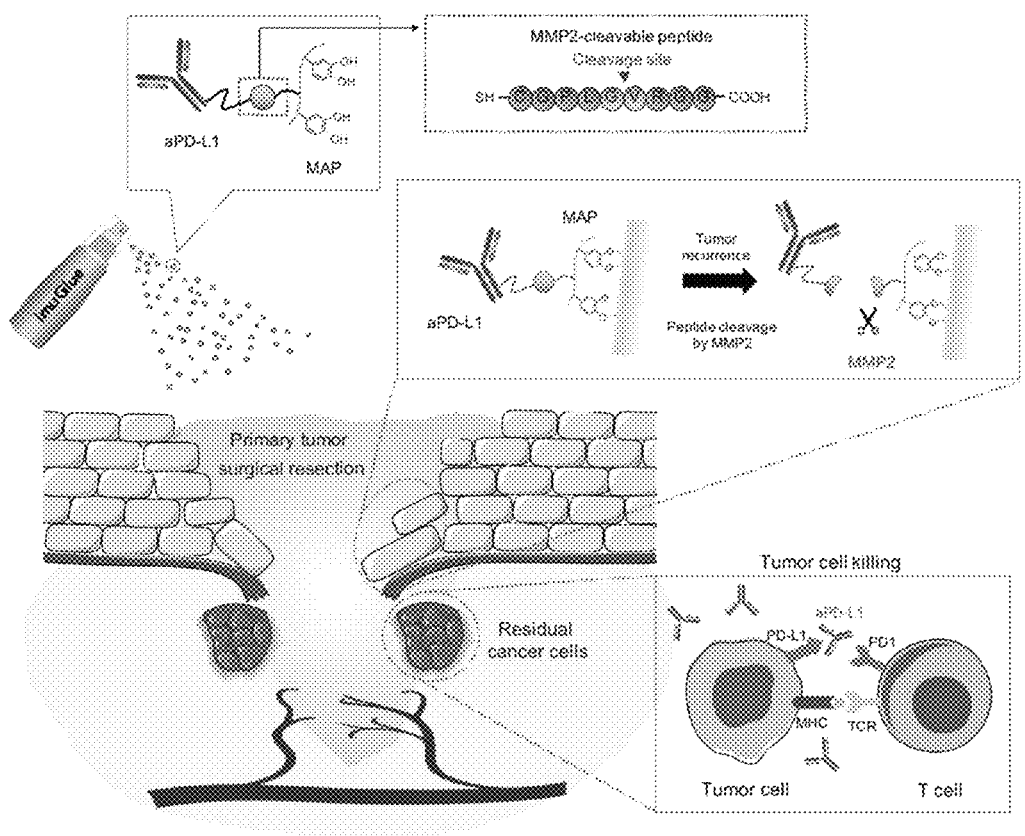
FIG. 10 is a diagram schematically showing the imuGlue spray system according to the present disclosure as used in cancer immunotherapy.

As shown in FIGS. 9B and 9C, mice treated with MAP-aPD-L1 and 1-MT had significantly delayed tumor growth compared to other experimental groups. However, in the combination treatment of free aPD-L1 and 1-MT, the released drug rapidly spread to other tissues and did not induce a synergistic anti-tumor effect when compared to free aPD-L1 alone treatment. Further, it was identified based on a result of weighing that there were no obvious signs of toxicity due to the combination treatment (FIG. 9D). The immunofluorescence image indicated that the combination treatment of MAP-aPD-L1 and 1-MT significantly increased infiltration of CD8+ T cells into tumor (FIG. 9E). It was identified based on the above result that the combination therapy via topical codelivery of imuGlue and 1-MT may effectively induce a T cell-mediated anti-tumor immune response.

The above experimental results indicate that the imuGlue according to the present disclosure increases the retention time of the antibody at the site of primary tumor resection and enables in situ release of antibodies in response to tumor growth. Further, the antibody released as needed maintains a high level of bioactivity and effectively binds to the tumor antigen. Thus, the anti-tumor effect may be substantially improved after surgery to prevent recurrence of cancer. In addition, the imuGlue may be applied in the form of the intratumoral injection in addition to the spray form, and thus may be usefully used for the treatment of unresectable local metastatic cancer. The imuGlue may enhance the T cell-mediated anti-tumor immunity. Thus, when used in combination with other immunotherapies such as a single immune checkpoint inhibitor (ICI) drug, the imuGlue may effectively induce the T cell-mediated anti-tumor immune response.

As a result, the bio-responsive adhesive antibody delivery platform according to the present disclosure improves the antibody delivery rate at the target site via the adhesiveness of a mussel adhesive protein, and specifically reacts with enzymes to specifically release antibodies therefrom for efficient immunotherapy. Thus, the bio-responsive adhesive antibody delivery platform may be useful as a new platform in various immunotherapies including anti-cancer immunity.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A mussel adhesive protein (MAP)-antibody (MAP-Ab) conjugate comprising a MAP and an anti-cancer antibody,
   wherein the MAP is conjugated to the N-terminus of a peptide;
   wherein the anti-cancer antibody is conjugated to the C-terminus of the peptide;
   wherein the peptide is cleavable by a matrix metalloproteinase-2 (MMP2);
   wherein the peptide has the amino acid sequence set forth in SEQ ID NO: 12,
   wherein the anti-cancer antibody inhibits a surface protein of a cancer cell;
   wherein when the MAP-Ab conjugate is exposed to an MMP2, the anti-cancer antibody is released therefrom; and
   wherein the amino acid sequence of the MAP is selected from the group consisting of SEQ ID NO:1, SEQ ID NO:2, SEQ ID NO:3, SEO ID NO: 4, SEQ ID NO:5, SEQ ID NO:6, SEQ ID NO:7, SEQ ID NO:8, SEQ ID NO:9, SEQ ID NO: 10, SEQ ID NO: 11, and any combination thereof.

2. The MAP-Ab conjugate of claim 1, wherein the antibody is directly coupled to, or is coupled by a linker to, a cysteine positioned at the N-terminus of the peptide.

3. The MAP-Ab conjugate of claim 1, wherein the anti-cancer antibody is selected from the group consisting of:
   i) an anti-PD-L1 antibody or an antigen-binding fragment thereof;
   ii) an anti-CTLA4 antibody or an antigen-binding fragment thereof;
   iii) an anti-LAG-3 antibody or an antigen-binding fragment thereof;
   iv) an anti-OX40 antibody or an antigen-binding fragment thereof;
   v) an anti-TIM3 antibody or an antigen-binding fragment thereof;
   vi) an anti-PD-1 antibody or an antigen-binding fragment thereof; and
   vii) any combination thereof.

4. An immunotherapy composition comprising an antibody and the MAP-Ab conjugate of claim 1.

5. The immunotherapy composition of claim 4, wherein the immunotherapy composition is disposed within a pharmaceutical composition.

6. The pharmaceutical composition of claim 5, further comprising an indoleamine (2,3)-dioxygenase (IDO) inhibitor.

7. The immunotherapy composition of claim 4, wherein the immunotherapy composition is disposed within an anti-cancer adjuvant.

8. A method for treating a solid cancer in a subject comprising administering to the subject a pharmaceutical composition comprising the immunotherapy composition of claim 4 by intratumoral injection.

9. The method of claim 8, wherein the cancer is selected from the group consisting of skin cancer, melanoma, gastric cancer, esophageal cancer, colon cancer, rectal colon cancer, pancreatic cancer, colorectal cancer, rectal cancer, bile duct cancer, liver cancer, brain tumor, sarcoma, bone cancer, breast cancer, thyroid cancer, lung adenocarcinoma, uterine cancer, cervical cancer, endometrial cancer, prostate cancer, head and neck cancer, bladder cancer, endocrine cancer, urethral cancer, ovarian cancer, testicular cancer, kidney cancer, and any combination thereof.

10. The method of claim 8, wherein the pharmaceutical composition is administered in combination with an IDO (indoleamine (2,3)-dioxygenase) inhibitor.

11. The MAP-Ab conjugate of claim 3, wherein the anti-cancer antibody comprises an anti-PD-L1 antibody or an antigen-binding fragment thereof.

12. The method of claim 10, wherein the IDO inhibitor comprises 1-methyl-tryptophan or NLG919.

* * * * *

SEQUENCE LISTING

```
<160> NUMBER OF SEQ ID NOS: 16

<210> SEQ ID NO 1
<211> LENGTH: 800
<212> TYPE: PRT
<213> ORGANISM: Artificial Sequence
<220> FEATURE:
<223> OTHER INFORMATION: fp-1

<400> SEQUENCE: 1

Ala Lys Pro Ser Tyr Pro Pro Thr Tyr Lys Ala Lys Pro Ser Tyr Pro
1               5                   10                  15

Pro Thr Tyr Lys Ala Lys Pro Ser Tyr Pro Pro Thr Tyr Lys Ala Lys
                20                  25                  30

Pro Ser Tyr Pro Pro Thr Tyr Lys Ala Lys Pro Ser Tyr Pro Pro Thr
            35                  40                  45

Tyr Lys Ala Lys Pro Ser Tyr Pro Pro Thr Tyr Lys Ala Lys Pro Ser
        50                  55                  60

Tyr Pro Pro Thr Tyr Lys Ala Lys Pro Ser Tyr Pro Pro Thr Tyr Lys
65                  70                  75                  80

Ala Lys Pro Ser Tyr Pro Pro Thr Tyr Lys Ala Lys Pro Ser Tyr Pro
                85                  90                  95

Pro Thr Tyr Lys Ala Lys Pro Ser Tyr Pro Pro Thr Tyr Lys Ala Lys
                100                 105                 110

Pro Ser Tyr Pro Pro Thr Tyr Lys Ala Lys Pro Ser Tyr Pro Pro Thr
            115                 120                 125

Tyr Lys Ala Lys Pro Ser Tyr Pro Pro Thr Tyr Lys Ala Lys Pro Ser
        130                 135                 140

Tyr Pro Pro Thr Tyr Lys Ala Lys Pro Ser Tyr Pro Pro Thr Tyr Lys
145                 150                 155                 160

Ala Lys Pro Ser Tyr Pro Pro Thr Tyr Lys Ala Lys Pro Ser Tyr Pro
                165                 170                 175

Pro Thr Tyr Lys Ala Lys Pro Ser Tyr Pro Pro Thr Tyr Lys Ala Lys
```

```
                    180                 185                 190
Pro Ser Tyr Pro Pro Thr Tyr Lys Ala Lys Pro Ser Tyr Pro Pro Thr
            195                 200                 205

Tyr Lys Ala Lys Pro Ser Tyr Pro Pro Thr Tyr Lys Ala Lys Pro Ser
        210                 215                 220

Tyr Pro Pro Thr Tyr Lys Ala Lys Pro Ser Tyr Pro Pro Thr Tyr Lys
225                 230                 235                 240

Ala Lys Pro Ser Tyr Pro Pro Thr Tyr Lys Ala Lys Pro Ser Tyr Pro
                245                 250                 255

Pro Thr Tyr Lys Ala Lys Pro Ser Tyr Pro Pro Thr Tyr Lys Ala Lys
            260                 265                 270

Pro Ser Tyr Pro Pro Thr Tyr Lys Ala Lys Pro Ser Tyr Pro Pro Thr
        275                 280                 285

Tyr Lys Ala Lys Pro Ser Tyr Pro Pro Thr Tyr Lys Ala Lys Pro Ser
290                 295                 300

Tyr Pro Pro Thr Tyr Lys Ala Lys Pro Ser Tyr Pro Pro Thr Tyr Lys
305                 310                 315                 320

Ala Lys Pro Ser Tyr Pro Pro Thr Tyr Lys Ala Lys Pro Ser Tyr Pro
                325                 330                 335

Pro Thr Tyr Lys Ala Lys Pro Ser Tyr Pro Pro Thr Tyr Lys Ala Lys
            340                 345                 350

Pro Ser Tyr Pro Pro Thr Tyr Lys Ala Lys Pro Ser Tyr Pro Pro Thr
        355                 360                 365

Tyr Lys Ala Lys Pro Ser Tyr Pro Pro Thr Tyr Lys Ala Lys Pro Ser
370                 375                 380

Tyr Pro Pro Thr Tyr Lys Ala Lys Pro Ser Tyr Pro Pro Thr Tyr Lys
385                 390                 395                 400

Ala Lys Pro Ser Tyr Pro Pro Thr Tyr Lys Ala Lys Pro Ser Tyr Pro
                405                 410                 415

Pro Thr Tyr Lys Ala Lys Pro Ser Tyr Pro Pro Thr Tyr Lys Ala Lys
            420                 425                 430

Pro Ser Tyr Pro Pro Thr Tyr Lys Ala Lys Pro Ser Tyr Pro Pro Thr
        435                 440                 445

Tyr Lys Ala Lys Pro Ser Tyr Pro Pro Thr Tyr Lys Ala Lys Pro Ser
        450                 455                 460

Tyr Pro Pro Thr Tyr Lys Ala Lys Pro Ser Tyr Pro Pro Thr Tyr Lys
465                 470                 475                 480

Ala Lys Pro Ser Tyr Pro Pro Thr Tyr Lys Ala Lys Pro Ser Tyr Pro
                485                 490                 495

Pro Thr Tyr Lys Ala Lys Pro Ser Tyr Pro Pro Thr Tyr Lys Ala Lys
            500                 505                 510

Pro Ser Tyr Pro Pro Thr Tyr Lys Ala Lys Pro Ser Tyr Pro Pro Thr
        515                 520                 525

Tyr Lys Ala Lys Pro Ser Tyr Pro Pro Thr Tyr Lys Ala Lys Pro Ser
        530                 535                 540

Tyr Pro Pro Thr Tyr Lys Ala Lys Pro Ser Tyr Pro Pro Thr Tyr Lys
545                 550                 555                 560

Ala Lys Pro Ser Tyr Pro Pro Thr Tyr Lys Ala Lys Pro Ser Tyr Pro
                565                 570                 575

Pro Thr Tyr Lys Ala Lys Pro Ser Tyr Pro Pro Thr Tyr Lys Ala Lys
            580                 585                 590

Pro Ser Tyr Pro Pro Thr Tyr Lys Ala Lys Pro Ser Tyr Pro Pro Thr
        595                 600                 605
```

Tyr Lys Ala Lys Pro Ser Tyr Pro Pro Thr Tyr Lys Ala Lys Pro Ser
              610                 615                 620

Tyr Pro Pro Thr Tyr Lys Ala Lys Pro Ser Tyr Pro Pro Thr Tyr Lys
625                 630                 635                 640

Ala Lys Pro Ser Tyr Pro Pro Thr Tyr Lys Ala Lys Pro Ser Tyr Pro
                645                 650                 655

Pro Thr Tyr Lys Ala Lys Pro Ser Tyr Pro Pro Thr Tyr Lys Ala Lys
              660                 665                 670

Pro Ser Tyr Pro Pro Thr Tyr Lys Ala Lys Pro Ser Tyr Pro Pro Thr
          675                 680                 685

Tyr Lys Ala Lys Pro Ser Tyr Pro Pro Thr Tyr Lys Ala Lys Pro Ser
          690                 695                 700

Tyr Pro Pro Thr Tyr Lys Ala Lys Pro Ser Tyr Pro Pro Thr Tyr Lys
705                 710                 715                 720

Ala Lys Pro Ser Tyr Pro Pro Thr Tyr Lys Ala Lys Pro Ser Tyr Pro
                725                 730                 735

Pro Thr Tyr Lys Ala Lys Pro Ser Tyr Pro Pro Thr Tyr Lys Ala Lys
              740                 745                 750

Pro Ser Tyr Pro Pro Thr Tyr Lys Ala Lys Pro Ser Tyr Pro Pro Thr
          755                 760                 765

Tyr Lys Ala Lys Pro Ser Tyr Pro Pro Thr Tyr Lys Ala Lys Pro Ser
          770                 775                 780

Tyr Pro Pro Thr Tyr Lys Ala Lys Pro Ser Tyr Pro Pro Thr Tyr Lys
785                 790                 795                 800

<210> SEQ ID NO 2
<211> LENGTH: 472
<212> TYPE: PRT
<213> ORGANISM: Artificial Sequence
<220> FEATURE:
<223> OTHER INFORMATION: fp-2

<400> SEQUENCE: 2

Leu Phe Ser Phe Phe Leu Leu Thr Cys Thr Gln Leu Cys Leu Gly
1               5                   10                  15

Thr Asn Arg Pro Asp Tyr Asn Asp Glu Glu Asp Tyr Lys Pro
              20                  25                  30

Pro Val Tyr Lys Pro Ser Pro Ser Lys Tyr Arg Pro Val Asn Pro Cys
              35                  40                  45

Leu Lys Lys Pro Cys Lys Tyr Asn Gly Val Cys Lys Pro Arg Gly Gly
          50                  55                  60

Ser Tyr Lys Cys Phe Cys Lys Gly Gly Tyr Tyr Gly Tyr Asn Cys Asn
65                  70                  75                  80

Leu Lys Asn Ala Cys Lys Pro Asn Gln Cys Lys Asn Lys Ser Arg Cys
              85                  90                  95

Val Pro Val Gly Lys Thr Phe Lys Cys Val Cys Arg Asn Gly Asn Phe
              100                 105                 110

Gly Arg Leu Cys Glu Lys Asn Val Cys Ser Pro Asn Pro Cys Lys Asn
          115                 120                 125

Asn Gly Lys Cys Ser Pro Leu Gly Lys Thr Gly Tyr Lys Cys Thr Cys
          130                 135                 140

Ser Gly Gly Tyr Thr Gly Pro Arg Cys Glu Val His Ala Cys Lys Pro
145                 150                 155                 160

Asn Pro Cys Lys Asn Lys Gly Arg Cys Phe Pro Asp Gly Lys Thr Gly
              165                 170                 175

Tyr Lys Cys Arg Cys Val Asp Gly Tyr Ser Gly Pro Thr Cys Gln Glu
            180                 185                 190

Asn Ala Cys Lys Pro Asn Pro Cys Ser Asn Gly Gly Thr Cys Ser Ala
            195                 200                 205

Asp Lys Phe Gly Asp Tyr Ser Cys Glu Cys Arg Pro Gly Tyr Phe Gly
210                 215                 220

Pro Glu Cys Glu Arg Tyr Val Cys Ala Pro Asn Pro Cys Lys Asn Gly
225                 230                 235                 240

Gly Ile Cys Ser Ser Asp Gly Ser Gly Gly Tyr Arg Cys Arg Cys Lys
            245                 250                 255

Gly Gly Tyr Ser Gly Pro Thr Cys Lys Val Asn Val Cys Lys Pro Thr
            260                 265                 270

Pro Cys Lys Asn Ser Gly Arg Cys Val Asn Lys Gly Ser Ser Tyr Asn
            275                 280                 285

Cys Ile Cys Lys Gly Gly Tyr Ser Gly Pro Thr Cys Gly Glu Asn Val
            290                 295                 300

Cys Lys Pro Asn Pro Cys Gln Asn Arg Gly Arg Cys Tyr Pro Asp Asn
305                 310                 315                 320

Ser Asp Asp Gly Phe Lys Cys Arg Cys Val Gly Gly Tyr Lys Gly Pro
            325                 330                 335

Thr Cys Glu Asp Lys Pro Asn Pro Cys Asn Thr Lys Pro Cys Lys Asn
            340                 345                 350

Gly Gly Lys Cys Asn Tyr Asn Gly Lys Ile Tyr Thr Cys Lys Cys Ala
            355                 360                 365

Tyr Gly Trp Arg Gly Arg His Cys Thr Asp Lys Ala Tyr Lys Pro Asn
            370                 375                 380

Pro Cys Val Val Ser Lys Pro Cys Lys Asn Arg Gly Lys Cys Ile Trp
385                 390                 395                 400

Asn Gly Lys Ala Tyr Arg Cys Lys Cys Ala Tyr Gly Tyr Gly Gly Arg
            405                 410                 415

His Cys Thr Lys Lys Ser Tyr Lys Lys Asn Pro Cys Ala Ser Arg Pro
            420                 425                 430

Cys Lys Asn Arg Gly Lys Cys Thr Asp Lys Gly Asn Gly Tyr Val Cys
            435                 440                 445

Lys Cys Ala Arg Gly Tyr Ser Gly Arg Tyr Cys Ser Leu Lys Ser Pro
            450                 455                 460

Pro Ser Tyr Asp Asp Asp Glu Tyr
465                 470

<210> SEQ ID NO 3
<211> LENGTH: 50
<212> TYPE: PRT
<213> ORGANISM: Artificial Sequence
<220> FEATURE:
<223> OTHER INFORMATION: fp-3

<400> SEQUENCE: 3

Pro Trp Ala Asp Tyr Tyr Gly Pro Lys Tyr Gly Pro Pro Arg Arg Tyr
1               5                   10                  15

Gly Gly Gly Asn Tyr Asn Arg Tyr Gly Arg Arg Tyr Gly Gly Tyr Lys
            20                  25                  30

Gly Trp Asn Asn Gly Trp Lys Arg Gly Arg Trp Gly Arg Lys Tyr Tyr
        35                  40                  45

Gly Ser
    50

<210> SEQ ID NO 4
<211> LENGTH: 750
<212> TYPE: PRT
<213> ORGANISM: Artificial Sequence
<220> FEATURE:
<223> OTHER INFORMATION: fp-4

<400> SEQUENCE: 4

```
Tyr Gly Arg Arg Tyr Gly Glu Pro Ser Gly Tyr Ala Asn Ile Gly His
 1               5                  10                  15

Arg Arg Tyr Tyr Glu Arg Ala Ile Ser Phe His Arg His Ser His Val
            20                  25                  30

His Gly His His Leu Leu His Arg His Val His Arg His Ser Val Leu
        35                  40                  45

His Gly His Val His Met His Arg Val Ser His Arg Ile Met His Arg
    50                  55                  60

His Arg Val Leu His Gly His Val His Arg His Arg Val Leu His Asn
65                  70                  75                  80

His Val His Arg His Ser Val Leu His Gly His Val His Arg His Arg
                85                  90                  95

Val Leu His Arg His Val His Arg His Asn Val Leu His Gly His Val
            100                 105                 110

His Arg His Arg Val Leu His Lys His Val His Asn His Arg Val Leu
        115                 120                 125

His Lys His Leu His Lys His Gln Val Leu His Gly His Val His Arg
    130                 135                 140

His Gln Val Leu His Lys His Val His Asn His Arg Val Leu His Lys
145                 150                 155                 160

His Leu His Lys His Gln Val Leu His Gly His Val His Thr His Arg
                165                 170                 175

Val Leu His Lys His Val His Lys His Arg Val Leu His Lys His Leu
            180                 185                 190

His Lys His Gln Val Leu His Gly His Ile His Thr His Arg Val Leu
        195                 200                 205

His Lys His Leu His Lys His Gln Val Leu His Gly His Val His Thr
    210                 215                 220

His Arg Val Leu His Lys His Val His Lys His Arg Val Leu His Lys
225                 230                 235                 240

His Leu His Lys His Gln Val Leu His Gly His Val His Met His Arg
                245                 250                 255

Val Leu His Lys His Val His Lys His Arg Val Leu His Lys His Val
            260                 265                 270

His Lys His Val Val His Lys His Val His Ser His Arg Val Leu
        275                 280                 285

His Lys His Val His Lys His Arg Val Glu His Gln His Val His Lys
    290                 295                 300

His His Val Leu His Arg His Val Ser His Val His Val His Ser
305                 310                 315                 320

His Val His Lys His Arg Val His Ser His Val His Lys His Asn
                325                 330                 335

Val Val His Ser His Val His Arg His Gln Ile Leu His Arg His Val
            340                 345                 350

His Arg His Gln Val Val His Arg His Val His Arg His Leu Ile Ala
        355                 360                 365
```

```
His Arg His Ile His Ser His Gln Ala Ala Val His Arg His Val His
        370                 375                 380
Thr His Phe Glu Gly Asn Phe Asn Asp Asp Gly Thr Asp Val Asn Leu
385                 390                 395                 400
Arg Ile Arg His Gly Ile Ile Tyr Phe Gly Gly Asn Thr Tyr Arg Leu
                405                 410                 415
Ser Gly Gly Arg Arg Phe Met Thr Leu Trp Gln Glu Cys Leu Glu
            420                 425                 430
Ser Tyr Gly Asp Ser Asp Glu Cys Phe Val Gln Leu Leu Glu Gly Asn
        435                 440                 445
Gln His Leu Phe Thr Val Val Gln Gly His His Ser Thr Ser Phe Arg
    450                 455                 460
Ser Asp Leu Ser Asn Asp Leu His Pro Asp Asn Asn Ile Glu Gln Ile
465                 470                 475                 480
Ala Asn Asp His Val Asn Asp Ile Ala Gln Ser Thr Asp Gly Asp Ile
                485                 490                 495
Asn Asp Phe Ala Asp Thr His Tyr Asn Asp Val Ala Pro Ile Ala Asp
            500                 505                 510
Val His Val Asp Asn Ile Ala Gln Thr Ala Asp Asn His Val Lys Asn
        515                 520                 525
Ile Ala Gln Thr Ala His His His Val Asn Asp Val Ala Gln Ile Ala
    530                 535                 540
Asp Asp His Val Asn Asp Ile Gly Gln Thr Ala Tyr Asp His Val Asn
545                 550                 555                 560
Asn Ile Gly Gln Thr Ala Asp Asp His Val Asn Asp Ile Ala Gln Thr
                565                 570                 575
Ala Asp Asp His Val Asn Ala Ile Ala Gln Thr Ala Asp His Val
            580                 585                 590
Asn Ala Ile Ala Gln Thr Ala Asp Asp His Val Asn Asp Ile Gly Asp
        595                 600                 605
Thr Ala Asn Ser His Ile Val Arg Val Gln Gly Val Ala Lys Asn His
    610                 615                 620
Leu Tyr Gly Ile Asn Lys Ala Ile Gly Lys His Ile Gln His Leu Lys
625                 630                 635                 640
Asp Val Ser Asn Arg His Ile Glu Lys Leu Asn Asn His Ala Thr Lys
                645                 650                 655
Asn Leu Leu Gln Ser Ala Leu Gln His Lys Gln Gln Thr Ile Glu Arg
            660                 665                 670
Glu Ile Gln His Lys Arg His Leu Ser Glu Lys Glu Asp Ile Asn Leu
        675                 680                 685
Gln His Glu Asn Ala Met Lys Ser Lys Val Ser Tyr Asp Gly Pro Val
    690                 695                 700
Phe Asn Glu Lys Val Ser Val Ser Asn Gln Gly Ser Tyr Asn Glu
705                 710                 715                 720
Lys Val Pro Val Leu Ser Asn Gly Gly Tyr Asn Gly Lys Val Ser
                725                 730                 735
Ala Leu Ser Asp Gln Gly Ser Tyr Asn Glu Gly Tyr Ala Tyr
            740                 745                 750

<210> SEQ ID NO 5
<211> LENGTH: 82
<212> TYPE: PRT
<213> ORGANISM: Artificial Sequence
<220> FEATURE:
```

<223> OTHER INFORMATION: fp-5

<400> SEQUENCE: 5

```
Lys His His His His His Ser Ser Glu Glu Tyr Lys Gly Gly Tyr
1               5                   10                  15

Tyr Pro Gly Asn Thr Tyr His Tyr His Ser Gly Gly Ser Tyr His Gly
            20                  25                  30

Ser Gly Tyr His Gly Gly Tyr Lys Gly Lys Tyr Gly Lys Ala Lys
        35                  40                  45

Lys Tyr Tyr Tyr Lys Tyr Lys Asn Ser Gly Lys Tyr Lys Tyr Leu Lys
    50                  55                  60

Lys Ala Arg Lys Tyr His Arg Lys Gly Tyr Lys Lys Tyr Gly Gly
65                  70                  75                  80

Ser Ser
```

<210> SEQ ID NO 6
<211> LENGTH: 103
<212> TYPE: PRT
<213> ORGANISM: Artificial Sequence
<220> FEATURE:
<223> OTHER INFORMATION: fp-6

<400> SEQUENCE: 6

```
Ile Ala Ala Leu Cys Gly Ile Val Lys Ser Ile Asp Ser Asp Asp Ser
1               5                   10                  15

Asp Tyr Asp Tyr Lys Gly Arg Gly Tyr Cys Thr Asn Lys Gly Cys Arg
            20                  25                  30

Ser Gly Tyr Asn Tyr Phe Gly Asn Gly Tyr Cys Lys Tyr Gly Glu
        35                  40                  45

Lys Ser Tyr Thr Tyr Asn Cys Asn Ser Tyr Ala Gly Cys Cys Leu Pro
    50                  55                  60

Arg Asn Pro Tyr Gly Lys Leu Lys Tyr Cys Thr Asn Lys Tyr Gly
65                  70                  75                  80

Cys Pro Asn Asn Tyr Tyr Phe Tyr Asn Asn Lys Gly Tyr Tyr Leu
                85                  90                  95

Glu His His His His His His
            100
```

<210> SEQ ID NO 7
<211> LENGTH: 200
<212> TYPE: PRT
<213> ORGANISM: Artificial Sequence
<220> FEATURE:
<223> OTHER INFORMATION: fp-151

<400> SEQUENCE: 7

```
Ala Lys Pro Ser Tyr Pro Pro Thr Tyr Lys Ala Lys Pro Ser Tyr Pro
1               5                   10                  15

Pro Thr Tyr Lys Ala Lys Pro Ser Tyr Pro Pro Thr Tyr Lys Ala Lys
            20                  25                  30

Pro Ser Tyr Pro Pro Thr Tyr Lys Ala Lys Pro Ser Tyr Pro Pro Thr
        35                  40                  45

Tyr Lys Ala Lys Pro Ser Tyr Pro Pro Thr Tyr Lys Pro Trp Ser Ser
    50                  55                  60

Glu Glu Tyr Lys Gly Gly Tyr Tyr Pro Gly Asn Thr Tyr His Tyr His
65                  70                  75                  80

Ser Gly Gly Ser Tyr His Gly Ser Gly Tyr His Gly Gly Tyr Lys Gly
                85                  90                  95
```

```
Lys Tyr Tyr Gly Lys Ala Lys Lys Tyr Lys Tyr Lys Asn Ser
            100                 105                 110

Gly Lys Tyr Lys Tyr Leu Lys Lys Ala Arg Lys Tyr His Arg Lys Gly
            115                 120                 125

Tyr Lys Lys Tyr Gly Gly Ser Ser Gly Ser Ala Lys Pro Ser Tyr
            130                 135                 140

Pro Pro Thr Tyr Lys Ala Lys Pro Ser Tyr Pro Thr Tyr Lys Ala
145                 150                 155                 160

Lys Pro Ser Tyr Pro Pro Thr Tyr Lys Ala Lys Pro Ser Tyr Pro Pro
                165                 170                 175

Thr Tyr Lys Ala Lys Pro Ser Tyr Pro Pro Thr Tyr Lys Ala Lys Pro
            180                 185                 190

Ser Tyr Pro Pro Thr Tyr Lys Leu
            195                 200

<210> SEQ ID NO 8
<211> LENGTH: 171
<212> TYPE: PRT
<213> ORGANISM: Artificial Sequence
<220> FEATURE:
<223> OTHER INFORMATION: fp-131

<400> SEQUENCE: 8

Ala Lys Pro Ser Tyr Pro Pro Thr Tyr Lys Ala Lys Pro Ser Tyr Pro
1               5                   10                  15

Pro Thr Tyr Lys Ala Lys Pro Ser Tyr Pro Pro Thr Tyr Lys Ala Lys
                20                  25                  30

Pro Ser Tyr Pro Pro Thr Tyr Lys Ala Lys Pro Ser Tyr Pro Pro Thr
            35                  40                  45

Tyr Lys Ala Lys Pro Ser Tyr Pro Pro Thr Tyr Lys Pro Trp Ala Asp
50                  55                  60

Tyr Tyr Gly Pro Lys Tyr Gly Pro Pro Arg Arg Tyr Gly Gly Gly Asn
65                  70                  75                  80

Tyr Asn Arg Tyr Gly Arg Arg Tyr Gly Gly Tyr Lys Gly Trp Asn Asn
                85                  90                  95

Gly Trp Lys Arg Gly Arg Trp Gly Arg Lys Tyr Tyr Gly Ser Ala Lys
            100                 105                 110

Pro Ser Tyr Pro Pro Thr Tyr Lys Ala Lys Pro Ser Tyr Pro Pro Thr
            115                 120                 125

Tyr Lys Ala Lys Pro Ser Tyr Pro Pro Thr Tyr Lys Ala Lys Pro Ser
            130                 135                 140

Tyr Pro Pro Thr Tyr Lys Ala Lys Pro Ser Tyr Pro Pro Thr Tyr Lys
145                 150                 155                 160

Ala Lys Pro Ser Tyr Pro Pro Thr Tyr Lys Leu
                165                 170

<210> SEQ ID NO 9
<211> LENGTH: 175
<212> TYPE: PRT
<213> ORGANISM: Artificial Sequence
<220> FEATURE:
<223> OTHER INFORMATION: fp-353

<400> SEQUENCE: 9

Pro Trp Ala Asp Tyr Tyr Gly Pro Lys Tyr Gly Pro Pro Arg Arg Tyr
1               5                   10                  15

Gly Gly Gly Asn Tyr Asn Arg Tyr Gly Arg Arg Tyr Gly Gly Tyr Lys
```

```
                20                  25                  30
Gly Trp Asn Asn Gly Trp Lys Arg Gly Arg Trp Gly Arg Lys Tyr Tyr
                35                  40                  45

Pro Trp Ser Ser Glu Glu Tyr Lys Gly Gly Tyr Tyr Pro Gly Asn Thr
50                  55                  60

Tyr His Tyr His Ser Gly Ser Tyr His Gly Ser Gly Tyr His Gly
65                  70                  75                  80

Gly Tyr Lys Gly Lys Tyr Tyr Gly Lys Ala Lys Lys Tyr Tyr Lys
                85                  90                  95

Tyr Lys Asn Ser Gly Lys Tyr Lys Tyr Leu Lys Lys Ala Arg Lys Tyr
                100                 105                 110

His Arg Lys Gly Tyr Lys Lys Tyr Tyr Gly Gly Ser Ser Gly Ser Ala
                115                 120                 125

Asp Tyr Tyr Gly Pro Lys Tyr Gly Pro Pro Arg Arg Tyr Gly Gly Gly
                130                 135                 140

Asn Tyr Asn Arg Tyr Gly Arg Arg Tyr Gly Gly Tyr Lys Gly Trp Asn
145                 150                 155                 160

Asn Gly Trp Lys Arg Gly Arg Trp Gly Arg Lys Tyr Tyr Gly Ser
                165                 170                 175

<210> SEQ ID NO 10
<211> LENGTH: 187
<212> TYPE: PRT
<213> ORGANISM: Artificial Sequence
<220> FEATURE:
<223> OTHER INFORMATION: fp-153

<400> SEQUENCE: 10

Ala Lys Pro Ser Tyr Pro Pro Thr Tyr Lys Ala Lys Pro Ser Tyr Pro
1               5                   10                  15

Pro Thr Tyr Lys Ala Lys Pro Ser Tyr Pro Pro Thr Tyr Lys Ala Lys
                20                  25                  30

Pro Ser Tyr Pro Pro Thr Tyr Lys Ala Lys Pro Ser Tyr Pro Pro Thr
                35                  40                  45

Tyr Lys Ala Lys Pro Ser Tyr Pro Pro Thr Tyr Lys Pro Trp Ser Ser
                50                  55                  60

Glu Glu Tyr Lys Gly Gly Tyr Tyr Pro Gly Asn Thr Tyr His Tyr His
65                  70                  75                  80

Ser Gly Gly Ser Tyr His Gly Ser Gly Tyr His Gly Gly Tyr Lys Gly
                85                  90                  95

Lys Tyr Tyr Gly Lys Ala Lys Lys Tyr Tyr Lys Tyr Lys Asn Ser
                100                 105                 110

Gly Lys Tyr Lys Tyr Leu Lys Lys Ala Arg Lys Tyr His Arg Lys Gly
                115                 120                 125

Tyr Lys Lys Tyr Tyr Gly Gly Ser Ser Gly Ser Ala Asp Tyr Tyr Gly
                130                 135                 140

Pro Lys Tyr Gly Pro Pro Arg Arg Tyr Gly Gly Gly Asn Tyr Asn Arg
145                 150                 155                 160

Tyr Gly Arg Arg Tyr Gly Gly Tyr Lys Gly Trp Asn Asn Gly Trp Lys
                165                 170                 175

Arg Gly Arg Trp Gly Arg Lys Tyr Tyr Gly Ser
                180                 185

<210> SEQ ID NO 11
<211> LENGTH: 187
<212> TYPE: PRT
```

<213> ORGANISM: Artificial Sequence
<220> FEATURE:
<223> OTHER INFORMATION: fp-351

<400> SEQUENCE: 11

Pro Trp Ala Asp Tyr Tyr Gly Pro Lys Tyr Gly Pro Arg Arg Tyr
1               5                   10                  15

Gly Gly Gly Asn Tyr Asn Arg Tyr Gly Arg Arg Tyr Gly Gly Tyr Lys
            20                  25                  30

Gly Trp Asn Asn Gly Trp Lys Arg Gly Arg Trp Gly Arg Lys Tyr Tyr
        35                  40                  45

Pro Trp Ser Ser Glu Glu Tyr Lys Gly Tyr Tyr Pro Gly Asn Thr
    50                  55                  60

Tyr His Tyr His Ser Gly Gly Ser Tyr His Gly Ser Gly Tyr His Gly
65                  70                  75                  80

Gly Tyr Lys Gly Lys Tyr Gly Lys Ala Lys Lys Tyr Tyr Lys
                85                  90                  95

Tyr Lys Asn Ser Gly Lys Tyr Lys Tyr Leu Lys Lys Ala Arg Lys Tyr
                100                 105                 110

His Arg Lys Gly Tyr Lys Lys Tyr Gly Gly Ser Ser Gly Ser Ala
            115                 120                 125

Lys Pro Ser Tyr Pro Pro Thr Tyr Lys Ala Lys Pro Ser Tyr Pro Pro
    130                 135                 140

Thr Tyr Lys Ala Lys Pro Ser Tyr Pro Pro Thr Tyr Lys Ala Lys Pro
145                 150                 155                 160

Ser Tyr Pro Pro Thr Tyr Lys Ala Lys Pro Ser Tyr Pro Pro Thr Tyr
                165                 170                 175

Lys Ala Lys Pro Ser Tyr Pro Pro Thr Tyr Lys
            180                 185

<210> SEQ ID NO 12
<211> LENGTH: 9
<212> TYPE: PRT
<213> ORGANISM: Artificial Sequence
<220> FEATURE:
<223> OTHER INFORMATION: MMP2-cleavable peptide

<400> SEQUENCE: 12

Cys Gly Pro Leu Gly Val Arg Gly Gly
1               5

<210> SEQ ID NO 13
<211> LENGTH: 8
<212> TYPE: PRT
<213> ORGANISM: Artificial Sequence
<220> FEATURE:
<223> OTHER INFORMATION: MMP2-cleavable peptide

<400> SEQUENCE: 13

Gly Pro Val Gly Leu Ile Gly Lys
1               5

<210> SEQ ID NO 14
<211> LENGTH: 8
<212> TYPE: PRT
<213> ORGANISM: Artificial Sequence
<220> FEATURE:
<223> OTHER INFORMATION: MMP2-cleavable peptide

```
<400> SEQUENCE: 14

Gly Pro Leu Gly Ile Ala Gly Gln
1               5

<210> SEQ ID NO 15
<211> LENGTH: 5
<212> TYPE: PRT
<213> ORGANISM: Artificial Sequence
<220> FEATURE:
<223> OTHER INFORMATION: MMP2-cleavable peptide

<400> SEQUENCE: 15

Gly Pro Leu Gly Val
1               5

<210> SEQ ID NO 16
<211> LENGTH: 6
<212> TYPE: PRT
<213> ORGANISM: Artificial Sequence
<220> FEATURE:
<223> OTHER INFORMATION: MMP2-cleavable peptide

<400> SEQUENCE: 16

Pro Val Gly Leu Ile Gly
1               5
```